(12) United States Patent
Schmitz

(10) Patent No.: US 8,941,830 B2
(45) Date of Patent: Jan. 27, 2015

(54) SYSTEMS AND METHODS FOR MEASURING OXYGENATION

(75) Inventor: Roger Schmitz, Hutchinson, MN (US)

(73) Assignee: Hutchinson Technology Incorporated, Hutchinson, MN (US)

( * ) Notice: Subject to any disclaimer, the term of this patent is extended or adjusted under 35 U.S.C. 154(b) by 0 days.

(21) Appl. No.: 14/007,574

(22) PCT Filed: Mar. 25, 2012

(86) PCT No.: PCT/US2012/030494
§ 371 (c)(1),
(2), (4) Date: Sep. 25, 2013

(87) PCT Pub. No.: WO2012/135079
PCT Pub. Date: Oct. 4, 2012

(65) Prior Publication Data
US 2014/0016132 A1    Jan. 16, 2014

Related U.S. Application Data

(60) Provisional application No. 61/467,945, filed on Mar. 25, 2011.

(51) Int. Cl.
*G01N 21/00*  (2006.01)
*G01N 33/483*  (2006.01)
(Continued)

(52) U.S. Cl.
CPC ........ *G01N 33/4833* (2013.01); *A61B 5/14551* (2013.01); *A61B 5/002* (2013.01); *A61B 5/0075* (2013.01); *A61B 5/6825* (2013.01); *A61B 5/6828* (2013.01)
USPC .......................................... 356/343; 356/338

(58) Field of Classification Search
USPC ............................. 356/343, 338, 39–42, 317; 600/475–478, 326, 364, 342, 310–316, 600/322–329
See application file for complete search history.

(56) References Cited

U.S. PATENT DOCUMENTS 6,304,767 B1    10/2001    Soller et al.
6,678,541 B1    1/2004    Durkin et al.
6,766,188 B2    7/2004    Soller (Continued)

OTHER PUBLICATIONS

United States International Searching Authority; International Search Report for PCT/US12/30494; issued Jul. 13, 2012; U.S. Patent and Trademark Office; Alexandria, VA; US.

(Continued)

*Primary Examiner* — Tri T Ton
(74) *Attorney, Agent, or Firm* — Underwood & Associates, LLC

(57) ABSTRACT

Systems and methods are described for measuring a tissue parameter such as % StO2 in a tissue sample. One such method includes receiving first and second scattered light intensity signals at unique locations on a selected region of tissue from light injected into the region of tissue from a light source to identify a measured light attenuation data value. An electronic data store can be accessed that includes simulated light attenuation data determined from a mathematical tissue model at discrete points over a range of two or more tissue parameters, where the simulated light attenuation data are a function of one or more temperature-dependent light source spectra. The tissue parameter in the tissue sample can be determined by selecting a closest match between the measured light attenuation data and the simulated light attenuation data. An electronic signal representative of the determined tissue parameter can be sent to an output register.

20 Claims, 15 Drawing Sheets

(51) Int. Cl.
*A61B 5/1455* (2006.01)
*A61B 5/00* (2006.01)

(56) References Cited

U.S. PATENT DOCUMENTS

| | | |
|---|---|---|
| 7,047,054 B2 | 5/2006 | Benni |
| 2005/0187488 A1 | 8/2005 | Wolf |
| 2006/0189861 A1 | 8/2006 | Chen et al. |
| 2009/0259117 A1 | 10/2009 | Wider et al. |
| 2010/0049016 A1 | 2/2010 | Aronowitz et al. |
| 2011/0060200 A1 | 3/2011 | Bernreuter |

OTHER PUBLICATIONS

United States International Searching Authority; Written Opinion of the International Searching Authority for PCT/US12/30494; issued Jul. 13, 2012; U.S. Patent and Trademark Office; Alexandria, VA; US.

Hutchinson Technology Incorporated; Response to the Written Opinion of the International Searching Authority filed for PCT/US12/30494; filed on Dec. 11, 2012; Brooklyn Park, MN; US.

United States International Preliminary Examination Authority; International Preliminary Report on Patentability for PCT/US12/30494; issued Jul. 25, 2013; U.S. Patent and Trademark Office; Alexandria, VA; US.

FIG. 1A

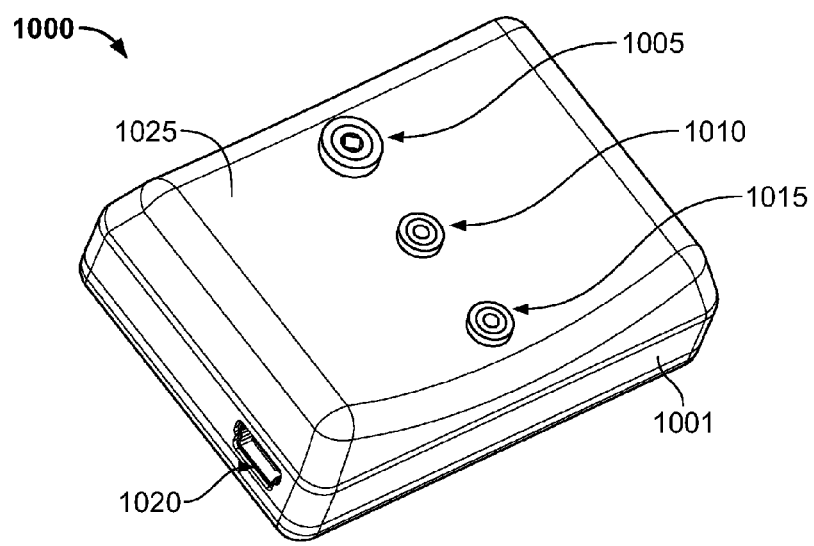
FIG. 10A
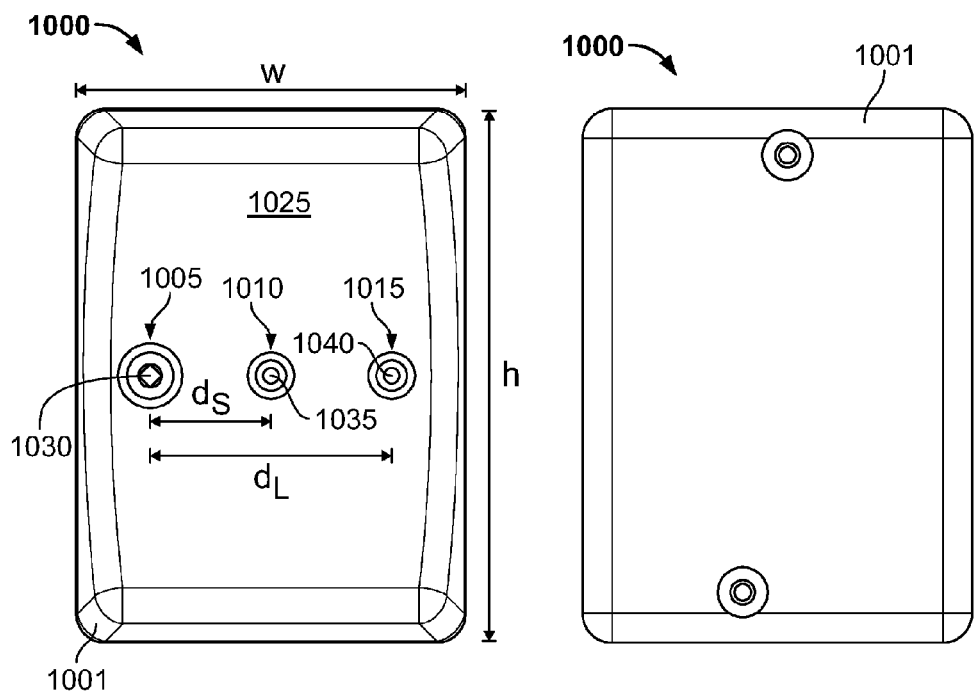
FIG. 10B
FIG. 10C

SYSTEMS AND METHODS FOR MEASURING OXYGENATION

CROSS REFERENCE TO RELATED APPLICATIONS

This application claims priority to and the benefit of U.S. Provisional Patent Application No. 61/467,945, filed on Mar. 25, 2011, the entire contents of which are incorporated herein by reference in their entirety.

TECHNICAL FIELD

This disclosure relates to systems and methods for measuring tissue oxygenation, in particular, through computer-implemented models.

BACKGROUND

Blood oxygen saturation is one of many parameters used to assess a patient's health, and in particular, the efficacy of their circulation and cardiovascular system. Oxygen saturation can be directly measured via invasive methods, e.g., by taking a sample of blood from the patient. However, portable oximetry systems allow non-invasive blood oxygen saturation measurement via reflectance or absorption measurements performed on or through a patient's skin or nailbeds, for example. Some oximetry systems determine blood oxygen saturation from the absorption of light by oxy- or deoxyhemoglobin in a tissue sample area.

SUMMARY

In one exemplary aspect, a system is described for measuring tissue oxygenation using a computer-implemented method as described herein.

In one exemplary aspect, a computer-implemented method for determining tissue oxygenation is described. The method includes the steps of generating path length data from a Monte Carle model; smoothing said path length data; generating a set of reflectance data; and determining tissue oxygenation from said reflectance data.

In one exemplary aspect, a method for measuring a tissue parameter in a tissue sample is provided. The method includes receiving first and second scattered light intensity signals at unique locations on a selected region of tissue from light injected into the region of tissue from a light source to identify a measured light attenuation data value. The method further includes accessing an electronic data store that includes simulated light attenuation data determined from a mathematical tissue model at discrete points over a range of two or more tissue parameters, wherein the simulated light attenuation data are a function of one or more temperature-dependent light source spectra. The method further includes determining the tissue parameter in the tissue sample by selecting a closest match between the measured light attenuation data and the simulated light attenuation data, and transmitting an electronic signal representative of the determined tissue parameter to an output register.

In one embodiment, the tissue parameter is a chromophore concentration within the tissue. In a related embodiment, the chromophore is oxyhemoglobin or deoxyhemoglobin.

In one embodiment, receiving first and second light signals includes receiving light signals generated by first and second photodiodes arranged in a confronting relationship with a surface of the tissue sample. In a related embodiment, the first and second photodiodes are linearly arranged with respect to the light source and evenly distributed such that the distance between the light source and the first photodiode is approximately one-half the distance between the light source and the second photodiode.

In one embodiment, the light source is the distal end of a solid, light-transmitting medium arranged in a confronting relationship with a surface of the tissue sample, and wherein a proximal end of the light-transmitting medium is in optical communication with one or more light sources. In a related embodiment, the light source is a light-emitting diode (LED) configured to emit light having a selected center wavelength and a selected spectral bandwidth. A related embodiment further includes a plurality of LEDs adjacently arranged so as to maximize light output coupling efficiency into the proximal end of the light-transmitting medium.

In one embodiment, the solid, light-transmitting medium is a substantially transparent, rectangular polycarbonate member having a proximal (light input) end and a distal (light output) end and a length/therebetween, wherein the polycarbonate member has a substantially square cross-section perpendicular to the length l.

In one embodiment, the two or more tissue parameters are selected from the group: % $StO_2$, adipose thickness, muscle thickness, dermis thickness, epidermis thickness, total hemoglobin concentration, melanin concentration, and water volume fraction.

In one embodiment, selecting a closest match between the measured light attenuation data and the simulated light attenuation data includes interpolation of the calculated light attenuation data based on a measured temperature of the light source.

In one embodiment, selecting a closest match between the measured light attenuation data and the calculated light attenuation data includes determining a ratio value of the first and the second scattered light intensity signals from the light source; receiving a temperature measurement of the light source; generating a temperature-corrected set of light attenuation data by interpolating the calculated light attenuation data based on the measured temperature; finding the closest match of the temperature-corrected set of light attenuation data in the electronic data store; forming a Jacobian matrix that includes the partial derivatives of each temperature-corrected light attenuation data point with respect to each of the tissue parameter values at the closest-match sensor value; and solving the system of n equations and n unknowns provided by the Jacobian matrix and the residual values between the closest-match sensor value and the measured light intensity signal to yield a correction value that can be applied to the determined chromophore concentration to increase the precision of the measurement.

In one embodiment, the light source is configured to project the output of two or more LEDs having different output light spectral profiles, and determining a ratio value of the first and the second scattered light intensity signals from the light source includes determining a ratio value of the first and the second scattered light intensity signals at each of the output light spectral profiles. A related embodiment further includes adding or subtracting the correction value to the tissue parameter.

In one embodiment, the tissue sample is tissue of a living organism.

In one embodiment, the tissue is the gastrocnemius muscle of the lower leg of a human.

In one embodiment, the method is executed in a continual loop so as to provide a data stream of chromophore concentration measurements on a tissue sample, wherein the data stream is sent to the output register to be displayed on a display device.

In one embodiment, the loop has a cycle rate between about 1 second and about 3 seconds.

In one exemplary aspect, a computer program product is provided, which is encoded on a computer-readable medium, and operable to cause one or more processors to perform operations for measuring a chromophore concentration in a tissue sample. The operations include receiving first and second scattered light intensity signals at unique locations on a selected region of tissue from light injected into the region of tissue from a light source to identify a measured light attenuation data value. The operations further include accessing an electronic data store including calculated light attenuation data determined from a mathematical tissue model at discrete points over a range of two or more tissue parameters, wherein the chromophore is one of the parameters, and wherein the light attenuation data are a function of one or more temperature-dependent light source spectra. The operations further include determining the chromophore concentration in the tissue sample by selecting a closest match between the measured light attenuation data and the calculated light attenuation data. The operations further include transmitting an electronic signal representative of the determined chromophore concentration to an output register.

In one exemplary aspect, a system for measuring a tissue parameter in a tissue sample is provided. The system includes a computer control system in signal communication with a remote sensing device. The remote sensing device includes a plurality of light sources operable to produce an output signal for each of the light sources successively, wherein each of the output signals has a different spectral profile than the other output signals, and wherein the plurality of light sources is cooperatively arranged with a light-transmitting medium that is configured to inject the output signals into the tissue sample at a selected injection area of the tissue sample. The remote sensing device further includes two or more light detectors arranged substantially collinear with the light source, where a distance from the light source to a first of the detectors is about one-half the distance of the light source to a second, different one of the detectors, and where each of the detectors is configured to receive the light signal after having propagating through the tissue, to measure an attenuated light value. In this system, the control system is operable to initiate said measurement of said attenuated light signals. In this system, the computer control system includes a processor in signal communication with a data store that includes simulated light attenuation values. The simulated light attenuation values are determined from a mathematical tissue model at discrete points over a range of two or more tissue parameters, where the simulated light attenuation values are a function of one or more temperature-dependent variables of the light source spectra. The system further includes an output register in signal communication with the processor that is configured to receive a processor-calculated tissue parameter value determined by selecting a closest match between the measured light attenuation value and the simulated light attenuation values.

Certain embodiments may include one or more advantages. For example, the systems and methods described herein can provide the ability to measure tissue oxygenation in substantially real time; in a related advantage, repeat measurement and tissue oxygenation measurements can be performed rapidly, e.g., in 2-second time intervals to provide continual updates to users. In certain embodiments, the sensor devices described herein incorporate inexpensive light sources such as light-emitting diodes (LEDs) while maintaining the ability to measure tissue oxygenation and other parameters with a high degree of precision and accuracy. In certain embodiments, the systems and method described herein provide the ability to measure tissue oxygenation and other tissue parameters at various locations on a human or animal subject using the same sensor, and without requiring extensive configuration changes. In certain embodiments, various tissue parameters can be measured using a single sensor configuration. In a fifth advantage, certain tissue parameters can be measured using LEDs that produce selected emission spectra in an absorbance profile of a target analyte. In certain embodiments, interpolation techniques described herein provide the ability to determine a tissue parameter such as % StO2 with a high degree of precision using a look-up table of minimal size. Various embodiments may exhibit substantially improved insensitivity to variations in the light source center wavelength due to, for example, temperature variations. Various implementations may be operable without interference filters, which may substantially reduce the cost, size, weight and/or widen the applicability of a sensor module, for example, to various parts of the body (e.g., arm, leg). In some examples, computational burden may be substantially reduced by implementation of an interpolation routine to refine a measurement estimate at run-time, which may permit substantially reduced data storage capacity requirements and/or computational delay to produce a measurement, for example. Design time computational time may be substantially reduced when generating an n-dimensional array of simulated sensor value data. For example, computation time may be substantially reduced by a factor of $p1*p2*p3* \ldots pN$ where p1, p2 etc. represent ratios of precision for each of n parameters that are allowed by using a coarse array and interpolating rather than using a fine array. In an illustrative example, if the desired $StO_2$ precision is 0.5% $StO_2$, then computation time may advantageously improve by a factor of 10 if the lookup table precision were 5% $StO_2$ and interpolated relative to a lookup table with 0.5% precision with no interpolation. Other advantages will be apparent to those skilled in the arts.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

The foregoing summary is illustrative only and is not intended to be in any way limiting. In addition to the illustrative aspects, embodiments, and features described above, further aspects, embodiments, and features will become apparent by reference to the drawings and the following detailed description and claims.

DESCRIPTION OF DRAWINGS

The present embodiments are illustrated by way of the figures of the accompanying drawings in which like references indicate similar elements, and in which:

Figure 1A:
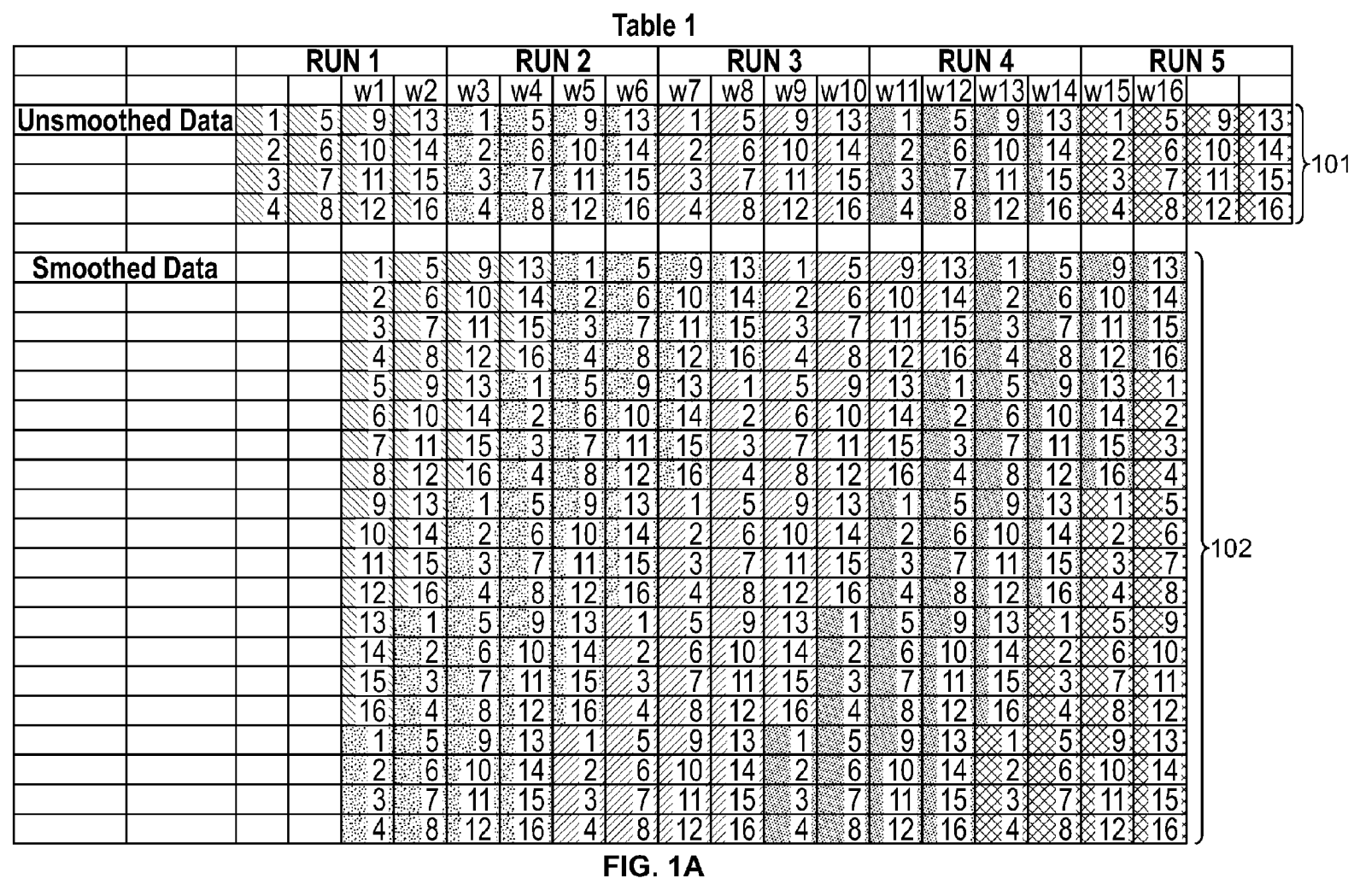

FIG. 1A is a table showing smoothed data, according to one embodiment;

FIGS. 10A-10H show various views of a sensor for measuring tissue oxygenation, according to one embodiment;

DETAILED DESCRIPTION OF ILLUSTRATIVE EMBODIMENTS

Figure 1B:
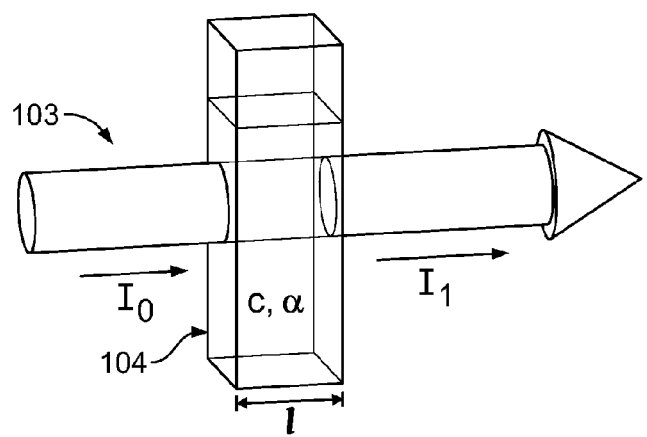
FIG. 1B is an illustration showing light passing through a medium, according to one embodiment.

In one general aspect, systems and methods are described for measuring a tissue parameter such as percent oxygen saturation (% $StO_2$). The system can include one or more sensors capable of outputting light from a light source at a first point on the tissue, and one or more light detectors at different locations, capable of receiving light signals after the light has propagated through a volume of the tissue. Given these data, computer-implemented methods can be carried out to determine the tissue parameter of interest.

In one exemplary embodiment, the computer implemented method includes a design-time step of creating a look-up table of calculated tissue data based on Monte Carlo simulations of light attenuation through the volume of tissue that is used later to compare with measured light attenuation data.

In one embodiment, a first design-time step includes performing Monte Carlo simulations based on a tissue model to produce simulated path length data of light rays as they propagate through the tissue, where the absorbance of the tissue is set to zero. The model can incorporate scattering properties and the geometry of the tissue, e.g., tissue layer thickness, shape, etc. so as to mimic the properties of the actual tissue being measured. Each Monte Carlo cycle can produce an output data set that includes a wavelength-dependent, two-dimensional data matrix including one row of data for each launched ray, and one column of path length data for each layer of tissue, with the total path length the ray traveled in that layer. The matrix can also include radius variable indicative of where the ray exited the model with respect to the injection point. The data matrix can be filtered to retain only path length data for rays of diffuse reflectance in the model and those that exited the model within a certain radius range. The filtered matrix resulting from each Monte Carlo simulation is referred to herein as the ray path length data matrix.

In one embodiment, a second design-time step includes smoothing the n-dimensional data matrices. One purpose for smoothing in this embodiment is to reduce the effects of variance errors that can be introduced by the statistical nature of the Monte Carlo method without having to simulate a larger number of rays that may otherwise be required for a desired level accuracy. The smoothing in this step is performed with respect to wavelength.

In one embodiment, a third design-time step includes using the smoothed ray path length data matrices to generate a matrix of the ratio of simulated light attenuation values at the two detector locations. The ratios in this matrix are calculated for each light source, using spectral properties for each light source at several chosen temperatures. The ratios are calculated at various discrete values of tissue parameters and sensor properties. The resulting matrix is referred to as the look-up table herein. The look-up table can include other parameters as described in greater detail below, to refine the process of determining an unknown tissue sample property.

In one embodiment, a first run-time step of the method includes receiving measured light intensity values from a remote sensor device and calculating the ratio of the intensities at the two detector locations; this ratio is a light attenuation value that is referred to as a "sensor value" herein. Next, the look-up table described above is loaded, and an interpolation step is performed based on temperature. Based on those data, the next step includes finding a "closest-match" set of sensor values in the look-up table that are closest to the simulated values. Next, another interpolation step is performed by calculating the values in the Jacobian matrix at the closest-match set of sensor values. Next, the residuals are calculated between the measured sensor values and the closest-match simulated sensor values. The Jacobian matrix is used along with these calculated residuals to determine the tissue parameter residuals associated with the closest-match sensor values. These tissue parameter residual values can be added to the closest-match tissue parameter values to arrive at the final determination of the tissue parameters of interest.

Additional run-time steps include sending the determined tissue parameter of interest to an output register so it can be stored for later retrieval, displayed on a viewing device such as a computer screen, or used in other desired ways.

The above steps are now described in greater detail.

The Monte Carlo method is known to be an accurate method for predicting the propagation of light through turbid tissue when the optical properties of the tissue are known. However, even with modern computer hardware, some Monte Carlo models can take several hours to several days to complete because they can be computationally intensive.

In one general aspect, a computer-implemented method for calculating one or more optical properties of a tissue is provided. In one embodiment of the method, a Monte Carlo model can be used to determine the optical properties of a tissue explicitly from a tissue measurement, such as a measurement of light attenuation as the light propagates through the tissue. As used herein, the term "light attenuation" as applied to measurement in tissue propagation refers to a decrease in light intensity measured at some point other than the light injection point, occurring as a result of absorption, scattering, or other like processes in the tissue. With reference to those skilled in the art of Monte Carlo simulations, this process is commonly referred to as "diffuse reflection" or, simply "reflection." It will be understood for purposes of describing the present illustrative embodiments that the terms light attenuation and reflection are generally interchangeable, while the former is considered to be a more scientifically rigorous term considering the configuration of the sensors described herein.

In one embodiment, a broad-band light source such as a light-emitting diode (LED) can be used as part of a system for collecting tissue reflectance data. It will be understood, however, that other light sources can be used. In some embodiments, LEDs can provide certain advantages, in that they can provide a broad band light source, as compared to, e.g., typical tissue chromophore absorption peaks. Some LEDs also provide the capability of a shiftable emission spectrum (e.g., center wavelength) as a function of junction temperature. In general, the algorithms described herein can accommodate variables in both wavelength and junction temperature.

In one embodiment, a method for calculating optical properties of tissues in "real time" from diffuse reflectance data in a target tissue includes using a Monte Carlo-based algorithm. For the sake of clarity, the steps of the algorithm in this embodiment are broken into four steps described below. It will be understood, however, that the steps can be executed in different order than that shown below, and that other steps can be included in the overall process. Such other steps will be apparent to those skilled in the art.

In this embodiment, the overall steps in the algorithm include: 1) generating calculated path length data from a Monte Carlo model; 2) mathematically smoothing the path length data generated in step 1); 3) generating a matrix of diffuse reflectance data at discrete values of tissue parameters and sensor optical properties; and 4) determining the tissue parameters (calculated tissue values) based on measured diffuse reflectance data (i.e., measured sensor values).

Step 1: Generate Path Length Data from Monte Carlo Models

In this embodiment, path length data is calculated using Monte Carlo simulations for the purpose of generating a look-up table of tissue vales that can be compared with measured sensor values. Path length data can be generated by running a Monte Carlo model of light propagating through layered tissue. In one approach, the model described by Wang et al. (Wang, L-H, S. L. Jacques, L-Q Zheng, "MCML—Monte Carlo modeling of photon transport in multi-layered tissues," Computer Methods and Programs in Biomedicine 47 (1995): 131-146) can be used; however, other models can be used.

In this embodiment, the actual path length traversed by a set of rays is generally dependent on the scattering properties and geometry of the tissue, e.g., tissue layer thickness, shape, and other features. A Monte Carlo model can be run with the absorption coefficients set to zero so that all rays must eventually exit the model. The Wang Monte Carlo routine can be modified so that the total path length of each ray in each layer, and the distance from the emitter to where the ray exits is recorded when it is output by the simulation.

In this embodiment, a Monte Carlo simulation can be executed for each scattering value and for each layer thickness of interest. For example, a simulation can be executed with four tissue layers representing epidermis, dermis, adipose, and muscle tissue, respectively. The simulation can be executed with exemplary fixed values, e.g., an epidermis thickness of 0.1 mm, a dermis thickness of 1.0 mm, muscle thickness of 50 mm, and 12 different values of adipose thickness ranging from, e.g., 1.0 mm to 20 mm. The simulation can also be executed with 15 different values of the scattering coefficient in each layer, representing the tissue optical properties from 590 nm to 890 nm. In this example, the simulation would perform 180 Monte Carlo cycles (12 different adipose thicknesses×15 different scattering coefficients), where about 1.2 million rays could be launched for each cycle.

In this embodiment, each Monte Carlo cycle can produce a two-dimensional (2D) data matrix including one row of data for each launched ray, and one column of data for each layer of tissue, with the total path length the ray traveled in that layer. There can also be a data column within the 2D matrix for a radius variable, representing the location from the point where the ray was launched to where the ray exited the model. Positive radius values can indicate diffuse reflectance and negative radius values can indicate diffuse transmission.

In this embodiment, upon completion of the 180 Monte Carlo cycles, the resulting 1.2 million rows of data can be filtered to retain only data for rays of diffuse reflectance and rays that exited the model within a certain radius range from the emitter. For example, rows that have positive radii between 11.75 mm and 13.25 mm could represent data for a 1.5 mm diameter detector positioned 12.5 mm from the emitter; rows that have positive radii between 24.25 mm and 25.75 mm could represent data for a 1.5 mm diameter detector positioned 25 mm from the emitter. The filtered matrices are the ray path length data matrices.

Step 2: Smooth the Path Length Data

In this embodiment, the second step of the algorithm includes combining the ray path length data matrices into a larger, smoothed matrix. The ray path length data matrix can be a two-dimensional data matrix including ray number and tissue layer.

Two detector locations and four tissue layers are considered in the description that follows. Additionally, 221 wavelengths are considered, representing a wavelength range from 630 nm to 850 nm, in 1 nm increments. In an illustrative example, the number of rays that can provide a satisfactory statistical representation for the Monte Carlo simulation appears to be about 35,360 for the short-spacing detector location and 12,376 for the long-spacing detector location in this embodiment.

In the description that follows, the desired number of rows for the data set is $n_{rows}$, the number of different values for the scattering coefficient is $n_s$, and the number of wavelengths is $n_\lambda$. Monte Carlo simulations were performed at $n_s=15$. In general, scattering changes smoothly and slowly over wavelength, so the data from the $n_s$ scattering runs can be smoothed over the 221 wavelengths. This results in:

$$\frac{n_\lambda}{n_s} = \text{\# of wavelength columns represented per model run} = n_{wpr} \quad (1)$$

It can be desirable in some cases to smooth the data over wavelength to reduce the effect of statistical Monte Carlo variations. In the description that follows, the smoothing factor SF is the number of columns of wavelength data that are shared. In most cases, SF should be an odd number to maintain symmetry. This gives:

$$\frac{n_{rows}}{SF} = \quad (2)$$

# of rays at each wavelength required before smoothing = $n_{rpw}$

Because the smoothing factor brings data in from wavelength columns on either side of any given column, additional data can be acquired below and above the 630 nm to 850 nm range so that wavelengths near the limits can also be smoothed.

The number of rays required per Monte Carlo simulation in this embodiment is $n_{wpr} \times n_{rpw} = n_{rpr}$. $n_s$ model cycles will produce $n_{rpr}$ rays per cycle; these data can be arranged for the smoothing function according to the following procedure, although other procedures can be used: first, arrange all of the data from $n_s \times n_{rpr}$ rays into a long column; next, group the rows into $n_{rpw}$ rows per group; next, assign a wavelength to each group (there will be $n_\lambda$ number of wavelengths in addition to the extra wavelengths required for smoothing); next, for each of the $n_\lambda$ wavelengths, select the group for that wavelength and the
(SF-1)/2 groups on either side. This will produce a matrix of $n_{rows} \times n_\lambda$, where $n_{rows}$ is the number of path length data rows and $n_\lambda$ is the number of wavelength columns.

Referring now to FIG. 1A, exemplary smoothing data is shown in Table 1. Table 1 shows the smoothing results of only a subset of the total Monte Carlo simulations, e.g., cycles 1-5, for clarity. The variables used in the smoothing data of Table 1 are: $n_s$=5, $n_\lambda$=16, SF=5, and $n_{rows}$=20, resulting in one smoothed data matrix for each adipose layer thickness. The top section 101 shows unsmoothed results for the five Monte Carlo cycles (five different scattering values). In this example, data for sixteen different wavelengths w1, w2, . . . w16 are sought. RUN1 unsmoothed data is the output of a Monte Carlo simulation at a certain scattering value; thus, in the smoothed data set 102, for w1, sixteen rays from RUN1 are utilized plus four rays from RUN2. Similarly, for w2, twelve rays from RUN1 are utilized and eight rays from RUN2. This approach continues for each wavelength. Each element of the unsmoothed data 101 is shown in a unique cell format to represent the scattering value of the unsmoothed data 101. The process can be advantageously used to provide weighted mixing of ray data so that the number of calculated scattering levels can be kept relatively low.

Step 3: Generate a Matrix of Diffuse Reflectance Data at Discrete Values of Tissue Parameters and Sensor Optical Properties Referring now to FIG. 1B, a light ray 103 is shown passing through a medium 104. The Beer-Lambert (B-L) Law and units are:

$$A = \ln\left(\frac{I_0}{I}\right) = \frac{\varepsilon c l}{M} \quad (3)$$

Figure 2:
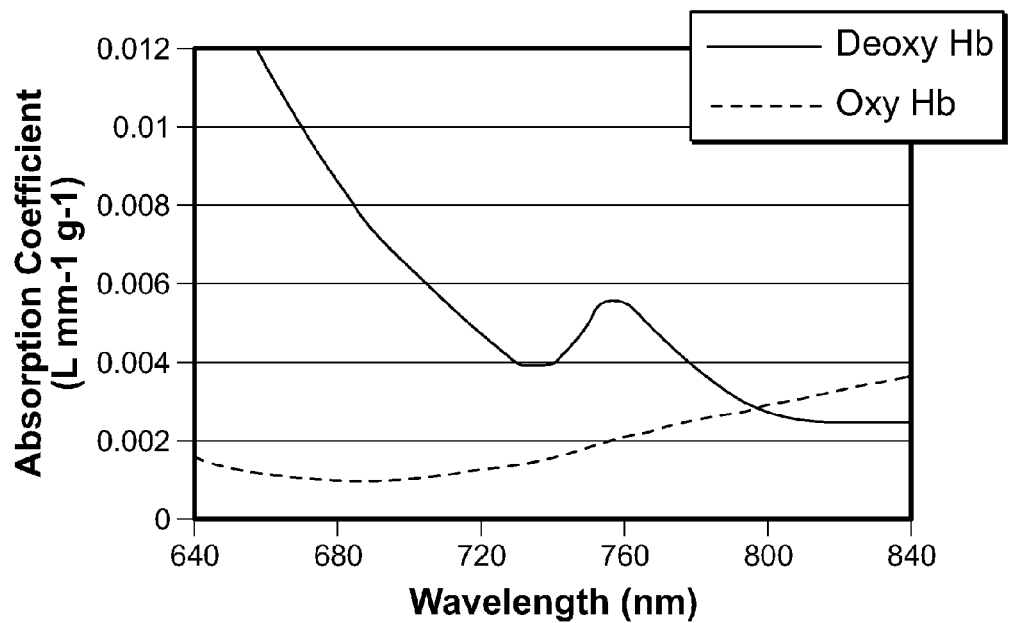
FIG. 2 is a chart showing oxy- and deoxy Hb absorbance curves.

$I_0$ and $I$ are the intensity of light at the input and output of the sample respectively, and $\varepsilon$ is the molar absorption coefficient, which is a property of the material being examined. $\varepsilon$ can be expressed as natural log (absorbance) per mm per micromolar. $\varepsilon$ can be converted to natural log (absorbance) per mm per molarity. M is the molecular weight of the material being examined in g/mole. Exemplary absorbance spectra for oxy- and deoxyhemoglobin (molecular weight 64,500 g/mole) are shown in FIG. 2. c is the concentration of the material being examined in g/L. l is the path length in the solution in mm. A can be expressed as (using the natural logarithm):

$$A = \frac{\varepsilon c l}{M} \quad (4)$$
$$= \frac{\frac{L}{mm \cdot mole} \cdot \frac{g}{L} \cdot mm}{\frac{g}{mole}}$$
$$= unitless$$

where $$\mu_A = \frac{\varepsilon c}{M}.$$

In general, five conditions should be met in order for the B-L law to be valid: 1) the absorbers should act independently of each other; 2) the absorbing medium should be homogeneously distributed in the interaction volume and should not scatter the radiation; 3) the incident radiation should consist of parallel rays, each traversing the same length in the absorbing medium; 4) the incident radiation should preferably be monochromatic, or have narrower bandwidth than the absorbing transition; and 5) the incident flux should not influence the atoms or molecules; it should only act as a non-invasive probe of the species under study. In particular, this implies that the light should not cause optical saturation or optical pumping, since such effects will deplete the lower level and possibly give rise to stimulated emission.

Light scatters as it propagates through tissue, so, in general not all rays traverse the same length. This phenomenon can be problematic when measuring chromophore concentrations in turbid media.

Figure 3:
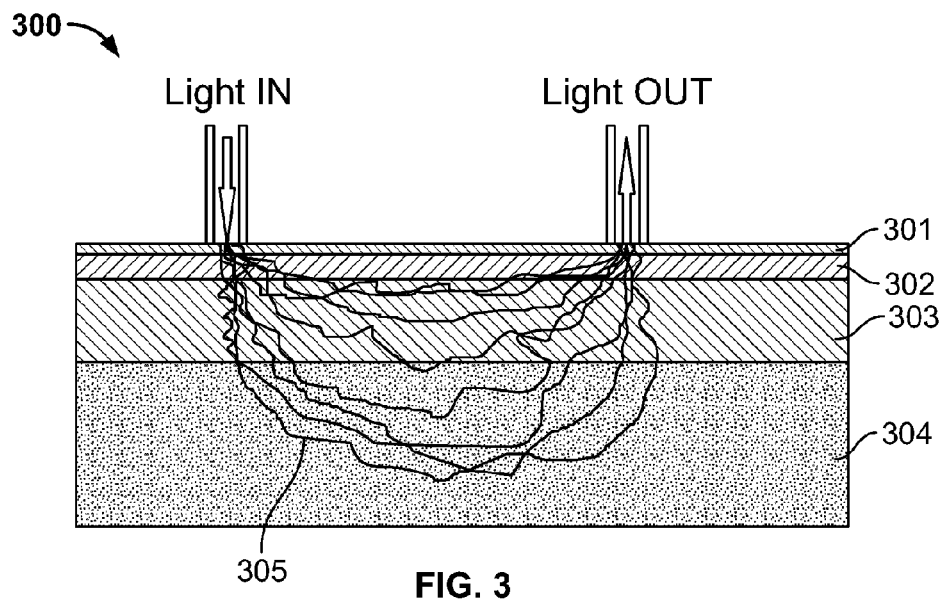
FIG. 3 is an illustration showing physiological structure and light passing therethrough, according to one embodiment.

Referring now to FIG. 3, consider a measurement media such as tissue 300 that has different optical properties in each of four different layers: an epidermis layer 301, a dermis layer 302, an adipose layer 303, and a muscle layer 304. When the light (illustrated by the jagged lines 305) passes through such layered media, it becomes evident that predicting the trajectory of light should be considered on a ray-by-ray basis. The path length distributions of rays in each layer cannot be considered independently, since rays with long paths in one layer might be biased to short paths in another layer.

In some cases, one or more of the validity conditions for the B-L law becomes problematic if a broad-band light source such as an LED is used. The spectral width of an LED can be on the order of 20-30 nm, which is comparable to the spectral width of hemoglobin absorbance features certain wavelength ranges (see FIG. 2). The absorption coefficients of hemoglobin can vary by nearly a factor of 2 over some 30 nm intervals; this should be considered in corresponding calculations. The Modified B-L equation is non-linear, so a simple weighted average may not be accurate.

This problem can be solved by integrating the Modified B-L law over wavelength. Consider that each broadband light output can be considered a combination of many narrow spectral bands with varying intensity that together form the broadband light output.

Figure 4:
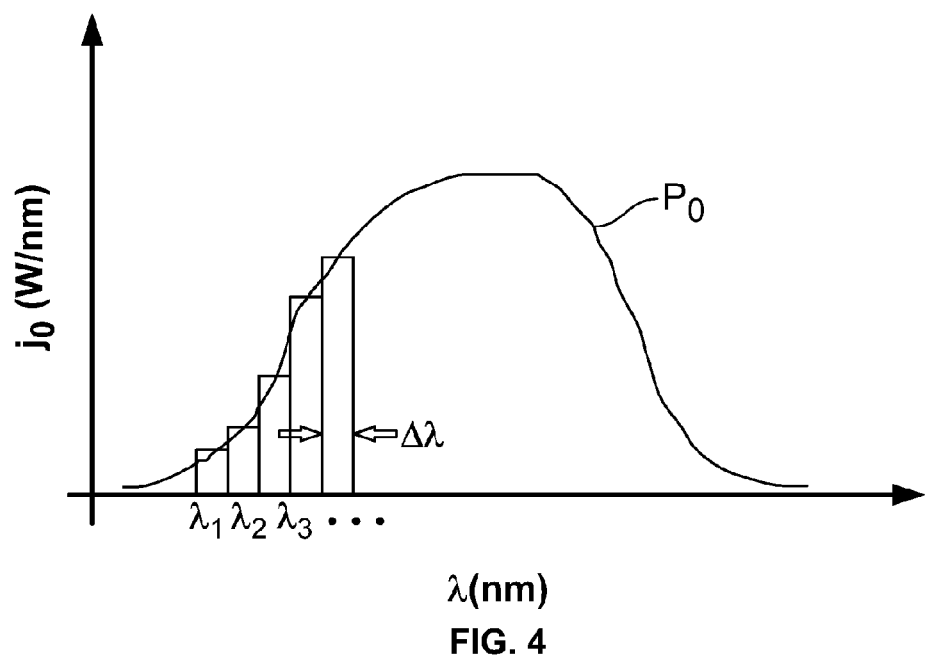
FIG. 4 is a chart illustrating total power input to a tissue sample, according to one embodiment.

Referring now to FIG. 4, an illustrative chart of total light power injected into a tissue is shown. The total power input to the tissue is the area under the curve $P_0$. For each wavelength interval $\Delta_\lambda$, the power input to the tissue can be given by:

$$h_{0,\lambda} = j_{0,\lambda}\Delta\lambda \quad (5)$$

$$P_0 = \sum_{\lambda=low}^{\lambda=high} h_{0,\lambda} \quad (6)$$
$$= \sum_{\lambda=low}^{\lambda=high} j_{0,\lambda}\Delta\lambda$$

Thus, in calculating ray data in this step of the algorithm, a separate Monte Carlo simulation can be executed for each wavelength interval to accommodate the changes in wavelength-depended scattering properties of the sample tissue.

Figure 5:
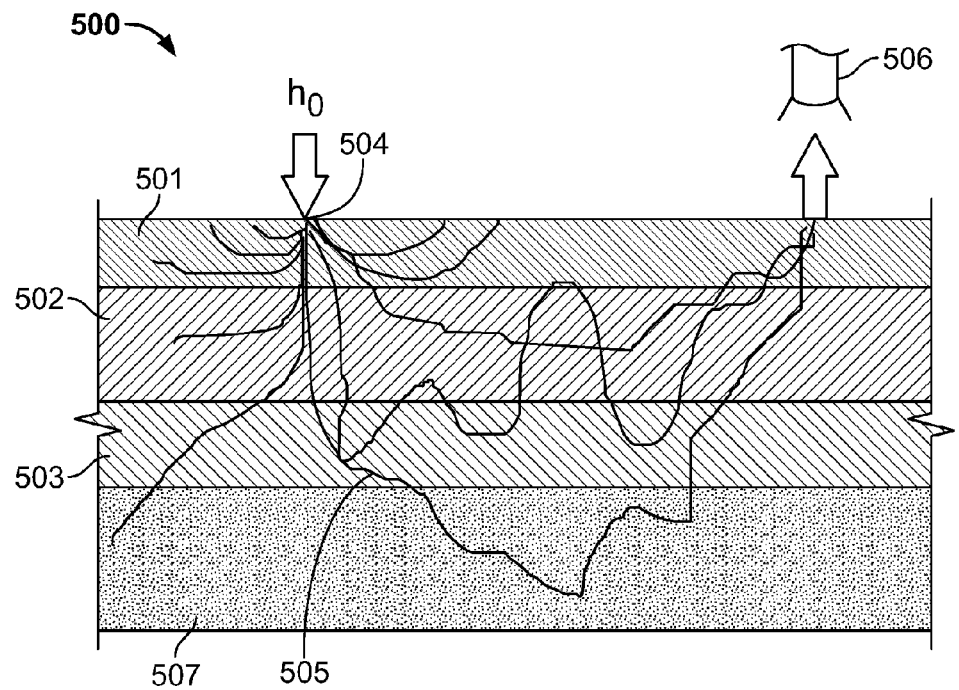
FIG. 5 is an illustration showing light propagation through layers of a medium, according to one embodiment.

Referring now to FIG. 5, in this embodiment, the first step in the Monte Carlo simulation is to inject a selected number of rays n into the modeled tissue 500. In this example, the tissue includes four layers, 501, 502, 503, 507 which can an epidermis, dermis, adipose, and muscle layer (denoted $L_e$, $L_d$, $L_a$, and $L_m$, respectively in the following equations). Rays are injected into the tissue 500 at an injection point 504. Each ray can be considered to have $k_{0,\lambda}=h_{0,\lambda}/n_\lambda=j_{0,\lambda}\Delta\lambda/n_\lambda$ power when it is injected into the model. In this model, the simulation produces a set of m rays that propagate through the tissue and reach the detector 506. Each ray will have a path length in each layer $L_e$, $L_d$, $L_a$, and $L_m$ (the jagged lines in FIG. 5 illustrate ray paths, e.g., ray path 505).

The absorbance of each individual ray (i) is given by:

$$A_i = \ln\left(\frac{k_{0,\lambda}}{k_{\lambda,i}}\right) = \mu_{A,e,\lambda}L_{e,\lambda,i} + \mu_{A,d,\lambda}L_{d,\lambda,i} + \mu_{A,a,\lambda}L_{a,\lambda,i} + \mu_{A,m,\lambda}L_{m,\lambda,i} \quad (7)$$

Next, the output power of each ray is solved:

$$k_{\lambda,i} = k_{0,\lambda}e^{-(\mu_{A,e,\lambda}L_{e,\lambda,i}+\mu_{A,d,\lambda}L_{d,\lambda,i}+\mu_{A,a,\lambda}L_{a,\lambda,i}+\mu_{A,m,\lambda}L_{m,\lambda,i})} \quad (8)$$

The total input power ($P_0$) is the sum of all $k_0$ injected rays:

$$P_0 = \sum_{\lambda=low}^{\lambda=high}\sum_{i=1}^{n_\lambda} \frac{j_{0,\lambda}\Delta\lambda}{n_\lambda} = \sum_{\lambda=low}^{\lambda=high} j_{0,\lambda}\Delta\lambda \quad (9)$$

The total output power (P) is the sum of all $k_{\lambda,i}$ rays that reach the detector:

$$P = \sum_{\lambda=low}^{\lambda=high}\sum_{i=1}^{m_\lambda} \frac{j_{0,\lambda}\Delta\lambda}{n_\lambda} e^{-(\mu_{A,e,\lambda}L_{e,\lambda,i}+\mu_{A,d,\lambda}L_{d,\lambda,i}+\mu_{A,a,\lambda}L_{a,\lambda,i}+\mu_{A,m,\lambda}L_{m,\lambda,i})} \quad (10)$$

Figure 6:
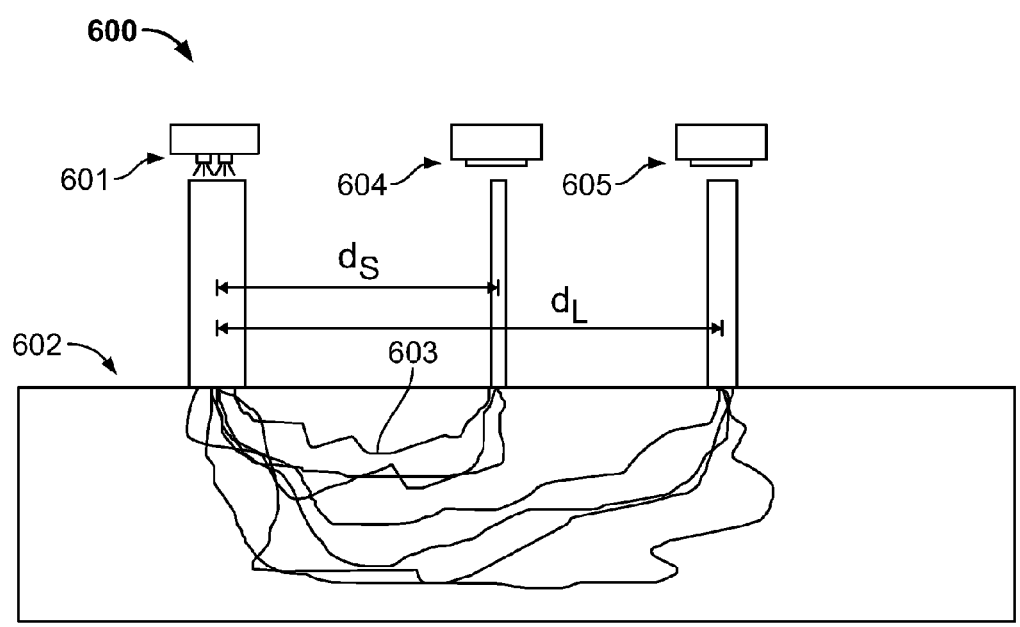
FIG. 6 is an illustration showing a light source, light propagating through a medium, and two photodiodes, according to one embodiment.

Referring now to FIG. 6, an exemplary tissue measurement system 600 is shown. In this example, the system includes a plurality of LEDs 601 configured to inject light into a tissue sample region 602 (no layers are indicated in FIG. 6 for clarity), where light rays are illustrated by way of the jagged lines, e.g., ray 603. The system 600 further includes a first light detector 604 and a second light detector 605. In some cases, for the reference reading, the instrument may not have the ability to measure the emitted power directly. For example, the light may be too intense and saturate the detector, making it difficult or impossible to precisely determine the intensity of the light at the detectors. Instead, a reference reading can be taken when the light is injected into an integrating sphere. The integrating sphere will have a reflectance versus wavelength curve of $\tau_\lambda$ which would have units of power-out per power-in per unit of detector area. The factor of $\tau_\lambda$ times the detector area ($a_{det}$) can be inserted into the above equation.

In some cases a photodetector may not have a spectrally flat sensitivity curve. In these circumstances intensity count readings can be adjusted by a sensitivity curve $S_\lambda$, having the units of counts/watt.

In general, the intensity output of LEDs can change with age and also according to operating temperature. The temperature-dependent spectral shape of an LED spectrum can be predicted relatively precisely; however, the temperature-dependent intensity may not be as easily predicted. The actual $j_{0,\lambda}$ curve will be some scalar multiple (p) of the curve predicted by a temperature compensation algorithm. The actual reference reading in counts can be expressed as:

$$I_0 = p\sum_{\lambda=low}^{\lambda=high} \tau_\lambda a_{det} S_\lambda j_{0,\lambda,ref}\Delta\lambda \quad (11)$$

Similar issues may occur with the sample reading; the photodetector may not have a spectrally flat sensitivity curve. In such situations the counts can be read according to a sensitivity curve $S_\lambda$, with the units of counts/watt.

The area of the detector used to measure intensity counts will, in most cases, be smaller than the modeled detection area in the Monte Carlo model. In general, large detectors are used in the Monte Carlo model to make it more time efficient; and smaller detectors are used on the sensor devices because they are generally more size- and cost effective. The actual counts on the detector will be reduced by the ratio of the detector area to the model area ($a_{ded}/a_{mod}$).

When the sample reading is taken, the efficiency of the optical coupling of the detector to the tissue is unknown. This is represented by a scalar factor f in the equations that follow. The actual sample reading in counts will be given by:

$$I = fq\frac{a_{det}}{a_{mod}}\sum_{\lambda=low}^{\lambda=high}\sum_{i=1}^{m_\lambda}\frac{S_\lambda j_{0,\lambda,samp}\Delta\lambda}{n_\lambda} \quad (12)$$
$$e^{-(\mu_{A,e,\lambda}L_{e,\lambda,i}+\mu_{A,d,\lambda}L_{d,\lambda,i}+\mu_{A,a,\lambda}L_{a,\lambda,i}+\mu_{A,m,\lambda}L_{m,\lambda,i})}$$

Equations (11) and (12) can be divided:

$$\frac{I_0}{I} = \frac{p\sum_{\lambda=low}^{\lambda=high}\tau_\lambda S_\lambda j_{0,\lambda,ref}\Delta\lambda}{\frac{fq}{a_{mod}}\sum_{\lambda=low}^{\lambda=high}\sum_{i=1}^{m_\lambda}\frac{S_\lambda j_{0,\lambda,samp}\Delta\lambda}{n_\lambda}} \quad (13)$$
$$e^{-(\mu_{A,e,\lambda}L_{e,\lambda,i}+\mu_{A,d,\lambda}L_{d,\lambda,i}+\mu_{A,a,\lambda}L_{a,\lambda,i}+\mu_{A,m,\lambda}L_{m,\lambda,i})}$$

Now consider that, in some circumstances, a long- and a short-spaced reading can be taken simultaneously. Referring back to FIG. 6, a long-spaced reading can refer to a reading from the detector 605 distal to the plurality of LEDs 601; similarly, the short-spaced reading can refer to a reading from the detector 604 proximal to the plurality of LEDs 601. The lg and sh subscripts are added below. Since the readings can be taken at the same time, the values for p, r, and $j_0$ are the same for the long and short readings. The integrating sphere reflectance is the same for both spacings so it is shown without a spacing subscript. The layers are considered to each be homogeneous so the $\mu_A$ values do not have spacing subscripts. The set of rays reaching each detector can be different so the path lengths do have spacing subscripts. The detectors are assumed in this model to have different sensitivities, but an additional requirement will be added later.

$$\frac{I_{0,lg}}{I_{lg}} = \frac{p \sum\limits_{\lambda=low}^{\lambda=high} \tau_\lambda S_{\lambda,lg} j_{0,\lambda,ref} \Delta\lambda}{\frac{f_{lg} q}{a_{mod,lg}} \sum\limits_{\lambda=low}^{\lambda=high} \sum\limits_{i=1}^{m_{\lambda,lg}} \frac{S_{\lambda,lg} j_{0,\lambda,samp} \Delta\lambda}{n_{\lambda,lg}}} \quad (14)$$

$$e^{-(\mu_{A,e,\lambda} L_{e,\lambda,i,lg} + \mu_{A,d,\lambda} L_{d,\lambda,i,lg} + \mu_{A,a,\lambda} L_{a,\lambda,i,lg} + \mu_{A,m,\lambda} L_{m,\lambda,i,lg})}$$

$$\frac{I_{0,sh}}{I_{sh}} = \frac{p \sum\limits_{\lambda=low}^{\lambda=high} \tau_\lambda S_{\lambda,sh} j_{0,\lambda,ref} \Delta\lambda}{\frac{f_{sh} q}{a_{mod,sh}} \sum\limits_{\lambda=low}^{\lambda=high} \sum\limits_{i=1}^{m_{\lambda,sh}} \frac{S_{\lambda,sh} j_{0,\lambda,samp} \Delta\lambda}{n_{\lambda,sh}}} \quad (15)$$

$$e^{-(\mu_{A,e,\lambda} L_{e,\lambda,i,sh} + \mu_{A,d,\lambda} L_{d,\lambda,i,sh} + \mu_{A,a,\lambda} L_{a,\lambda,i,sh} + \mu_{A,m,\lambda} L_{m,\lambda,i,sh})}$$

The above two equations can be divided to help cancel out some of the common variables and constants:

$$\frac{\frac{I_{0,lg}}{I_{lg}}}{\frac{I_{0,sh}}{I_{sh}}} = \frac{\frac{p \sum\limits_{\lambda=low}^{\lambda=high} \tau_\lambda S_{\lambda,lg} j_{0,\lambda,ref} \Delta\lambda}{\frac{f_{lg} q}{a_{mod,lg}} \sum\limits_{\lambda=low}^{\lambda=high} \sum\limits_{i=1}^{m_{\lambda,lg}} \frac{S_{\lambda,lg} j_{0,\lambda,samp} \Delta\lambda}{n_{\lambda,lg}}} e^{-(\mu_{A,e,\lambda} L_{e,\lambda,i,lg} + \mu_{A,d,\lambda} L_{d,\lambda,i,lg} + \mu_{A,a,\lambda} L_{a,\lambda,i,lg} + \mu_{A,m,\lambda} L_{m,\lambda,i,lg})}}{\frac{p \sum\limits_{\lambda=low}^{\lambda=high} \tau_\lambda S_{\lambda,sh} j_{0,\lambda,ref} \Delta\lambda}{\frac{f_{sh} q}{a_{mod,sh}} \sum\limits_{\lambda=low}^{\lambda=high} \sum\limits_{i=1}^{m_{\lambda,sh}} \frac{S_{\lambda,sh} j_{0,\lambda,samp} \Delta\lambda}{n_{\lambda,sh}}} e^{-(\mu_{A,e,\lambda} L_{e,\lambda,i,sh} + \mu_{A,d,\lambda} L_{d,\lambda,i,sh} + \mu_{A,a,\lambda} L_{a,\lambda,i,sh} + \mu_{A,m,\lambda} L_{m,\lambda,i,sh})}} \quad (16)$$

If the requirement is added that the long and short detectors have the same sensitivities, the numerators in the right side of the equation exactly cancel out. The scalar q's also cancel. The remaining scalar values can be replaced by a single scalar unknown value as shown below. In some cases the two areas are actually known from the modeling, but they need not be carried forward because they can be rolled into the unknown f factors.

$$f = \frac{f_{sh} a_{mod,lg}}{f_{lg} a_{mod,sh}} \quad (17)$$

Equation (16) above now becomes:

$$\frac{I_{0,lg} I_{sh}}{I_{0,sh} I_{lg}} = \frac{e^{-(\mu_{A,e,\lambda} L_{e,\lambda,i,sh} + \mu_{A,d,\lambda} L_{d,\lambda,i,sh} + \mu_{A,a,\lambda} L_{a,\lambda,i,sh} + \mu_{A,m,\lambda} L_{m,\lambda,i,sh})} f \sum\limits_{\lambda=low}^{\lambda=high} \sum\limits_{i=1}^{m_{\lambda,sh}} \frac{S_\lambda j_{0,\lambda,samp} \Delta\lambda}{n_{\lambda,sh}}}{\sum\limits_{\lambda=low}^{\lambda=high} \sum\limits_{i=1}^{m_{\lambda,lg}} \frac{S_\lambda j_{0,\lambda,samp} \Delta\lambda}{n_{\lambda,lg}} e^{-(\mu_{A,e,\lambda} L_{e,\lambda,i,lg} + \mu_{A,d,\lambda} L_{d,\lambda,i,lg} + \mu_{A,a,\lambda} L_{a,\lambda,i,lg} + \mu_{A,m,\lambda} L_{m,\lambda,i,lg})}} \quad (18)$$

Equation (18) can become four separate equations when applied to four LEDs. The "1" subscript indicates values that are different for the four LEDs.

$$\frac{I_{0,lg,1} I_{sh,1}}{I_{0,sh,1} I_{lg,1}} = \frac{e^{-(\mu_{A,e,\lambda} L_{e,\lambda,i,sh} + \mu_{A,d,\lambda} L_{d,\lambda,i,sh} + \mu_{A,a,\lambda} L_{a,\lambda,i,sh} + \mu_{A,m,\lambda} L_{m,\lambda,i,sh})} f \sum\limits_{\lambda=low_1}^{\lambda=high_1} \sum\limits_{i=1}^{m_{\lambda,sh}} \frac{S_\lambda j_{0,\lambda,samp,1} \Delta\lambda}{n_{\lambda,sh}}}{\sum\limits_{\lambda=low_1}^{\lambda=high_1} \sum\limits_{i=1}^{m_{\lambda,lg}} \frac{S_\lambda j_{0,\lambda,samp,1} \Delta\lambda}{n_{\lambda,lg}} e^{-(\mu_{A,e,\lambda} L_{e,\lambda,i,lg} + \mu_{A,d,\lambda} L_{d,\lambda,i,lg} + \mu_{A,a,\lambda} L_{a,\lambda,i,lg} + \mu_{A,m,\lambda} L_{m,\lambda,i,lg})}} \quad (19)$$

The variables that do not have i subscripts can be removed from the ray sum, which may be beneficial for computational purposes:

$$\frac{I_{0,lg,1} I_{sh,1}}{I_{0,sh,1} I_{lg,1}} = \frac{e^{-(\mu_{A,e,\lambda} L_{e,\lambda,i,sh} + \mu_{A,d,\lambda} L_{d,\lambda,i,sh} + \mu_{A,a,\lambda} L_{a,\lambda,i,sh} + \mu_{A,m,\lambda} L_{m,\lambda,i,sh})} f \sum\limits_{\lambda=low_1}^{\lambda=high_1} \frac{S_\lambda j_{0,\lambda,samp,1} \Delta\lambda}{n_{\lambda,sh}} \sum\limits_{i=1}^{m_{\lambda,sh}}}{\sum\limits_{\lambda=low_1}^{\lambda=high_1} \frac{S_\lambda j_{0,\lambda,samp,1} \Delta\lambda}{n_{\lambda,lg}} \sum\limits_{i=1}^{m_{\lambda,lg}} e^{-(\mu_{A,e,\lambda} L_{e,\lambda,i,lg} + \mu_{A,d,\lambda} L_{d,\lambda,i,lg} + \mu_{A,a,\lambda} L_{a,\lambda,i,lg} + \mu_{A,m,\lambda} L_{m,\lambda,i,lg})}} \quad (20)$$

The absorption coefficient for the epidermis can be expressed according to eqn. (21) below. $F_{mel}$ is the volume fraction of melanin in the epidermis. $\mu_{mel}$ and $\mu_{skin}$ are obtained from known absorbance spectra for melanin and background absorption of epidermis:

$$\mu_{A,e,\lambda} = F_{mel} \mu_{mel,\lambda} + \mu_{skin,\lambda} \quad (21)$$

The absorption coefficient for the dermis can be expressed according to eqn. (22) below. A term can be added for hemoglobin in the dermis in certain embodiments.

$$\mu_{A,d,\lambda} = \mu_{skin,\lambda} \quad (22)$$

The absorption coefficient of adipose is generally known. Some variation in adipose layer thickness can be accommodated by assuming that the magnitude of the adipose layer absorbance varies linearly. For large ranges of adipose layer thickness, separate ray traces may be required.

$$\mu_{A,a,\lambda} = (adp) * \mu_{adipose,\lambda} \quad (23)$$

The absorption coefficient for the muscle layer is given by the following equation. The $\epsilon$ and M values can be obtained from literature values. The $c_{wtr}$ value is assumed to be 70% for muscle.

$$\mu_{A,m,\lambda} = \frac{\varepsilon_{Hb}C_{Hb}}{M_{Hb}} + \frac{\varepsilon_{HbO2}C_{HbO2}}{M_{HbO2}} + \frac{\varepsilon_{wtr}C_{wtr}}{M_{wtr}} + \mu_{muscle} \quad (24)$$

This results in four equations for each LED with four unknowns ($c_{hb}$, $c_{hbo2}$, f, adp).

As described above, the output spectra of the LEDs can change with temperature. Generally, the center wavelength moves about +0.15 nm/C and the spectrum broadens. Generally, at higher temperatures, the band gap energy decreases, which results in the emission shifting to longer wavelengths. The effect is generally accepted to be linear and directly related to the junction temperature of the LED. Once the LED is mounted in its housing, the thermal conductivity between the junction and the housing can be stable over time. This leads to using the housing temperature being an accurate predictor of the spectral output of the LED over its life. This can be accomplished in one approach by measuring the housing temperature and output spectrum at two different temperatures and using a linear morphing algorithm to estimate the actual spectrum at any temperature. The spectral profiles of an LED at two different temperatures are shown in FIG. 7.

Figure 7:
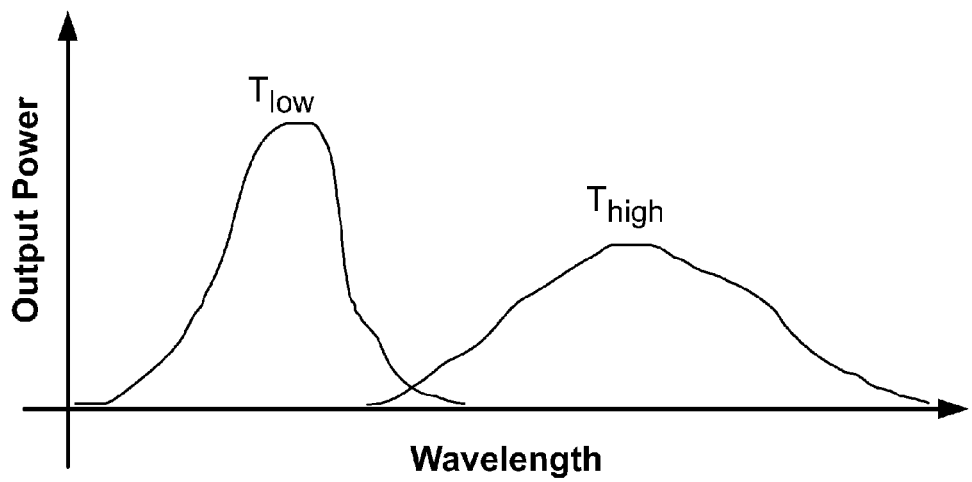
FIG. 7 is a chart of output power vs. wavelength, according to one embodiment.
Figure 8:
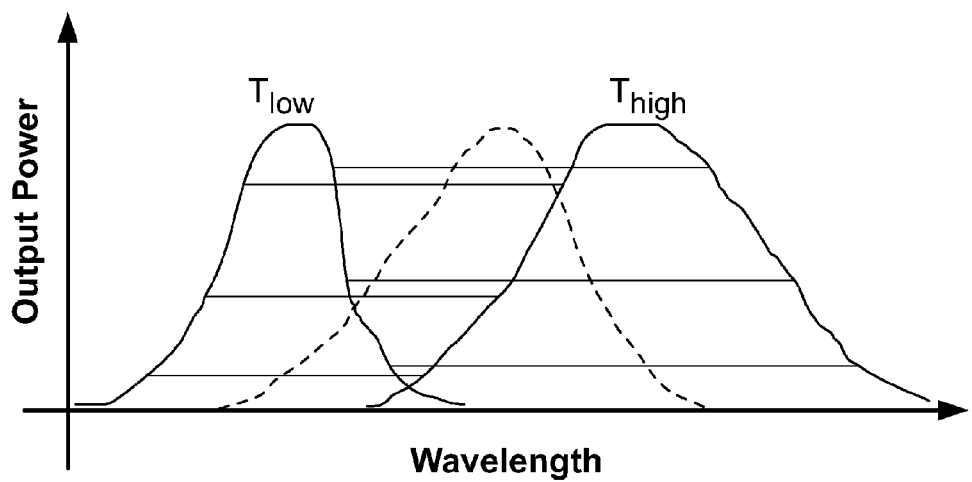
FIG. 8 is a chart of output power vs. wavelength.

Referring now to FIG. 8, the linear morphing can be accomplished in one approach by normalizing the two spectral profiles shown in FIG. 7, e.g., by scaling them vertically to have the same maximum value. The estimated curve can then be generated by interpolating the actual temperature along lines of constant normalized power.

The method described above can be used to generate a 2D matrix of data (the TVSV matrix). Every row in the matrix represents a set of tissue values and LED temperature. The TVSV matrix includes a column for every variable tissue property and sensor optical property. In this embodiment there are four columns for the modeled sensor values for each LED at those tissue parameters and sensor optical properties.

Tissue value simulations can be repeated at all temperatures to allow for interpolation later. For example, there could be a column for the tissue parameter of oxygenated hemoglobin concentration, deoxygenated hemoglobin concentration, and adipose layer thickness. Similarly, there could be data in the 2D matrix for the f factor and the LED temperature. In another approach, the TVSV matrix could include four columns that represent the following sensor value ratio for each LED:

$$\frac{I_{0,lg,1}I_{sh,1}}{I_{0,sh,1}I_{lg,1}} = SV_1 \quad (25)$$

In some cases, the tissue parameter columns can include $StO_2$, total hemoglobin concentration, and adipose layer thickness. In one example, sixteen additional columns can be added to the data set by numerically calculating the Jacobian matrix for the tissue parameter in each row. The Jacobian matrix can be based on the variation in the four sensor values based on variation in the three tissue parameters and the f factor.

Step 4: Determine the Tissue Parameters (Tissue Values) Based on Measured Diffuse Reflectance Data (Sensor Values)

In this embodiment, the algorithm further includes collecting sensor readings that include measured light output intensities measured on the tissue (referred to as sensor values (SV)) for each of the LEDs, along with the temperature of the LEDs. The data from the TVSV matrix can be (e.g., linearly) interpolated between temperature values based on the operational temperature of the LEDs. This results in an interpolated TVSV matrix with four columns for the three tissue parameters and the f factor, and four columns for the sensor values.

The four measured sensor values can be compared to the four sensor values in each row of the interpolated TVSV matrix to find the nearest set of values. The nearest set of values can be the set that has the smallest sum of squares of differences in sensor values.

Once the nearest set of tissue values is known, the precision can be refined by solving the following four equations and four unknowns:

$$\Delta SV_1 = \Delta TV_1 \frac{\partial SV_1}{\partial TV_1} + \Delta TV_2 \frac{\partial SV_1}{\partial TV_2} + \Delta TV_3 \frac{\partial SV_1}{\partial TV_3} + \Delta TV_4 \frac{\partial SV_1}{\partial TV_4} \quad (26)$$

$$\Delta SV_2 = \Delta TV_1 \frac{\partial SV_2}{\partial TV_1} + \Delta TV_2 \frac{\partial SV_2}{\partial TV_2} + \Delta TV_3 \frac{\partial SV_2}{\partial TV_3} + \Delta TV_4 \frac{\partial SV_2}{\partial TV_4} \quad (27)$$

$$\Delta SV_3 = \Delta TV_1 \frac{\partial SV_3}{\partial TV_1} + \Delta TV_2 \frac{\partial SV_3}{\partial TV_2} + \Delta TV_3 \frac{\partial SV_3}{\partial TV_3} + \Delta TV_4 \frac{\partial SV_3}{\partial TV_4} \quad (28)$$

$$\Delta SV_4 = \Delta TV_1 \frac{\partial SV_4}{\partial TV_1} + \Delta TV_2 \frac{\partial SV_4}{\partial TV_2} + \Delta TV_3 \frac{\partial SV_4}{\partial TV_3} + \Delta TV_4 \frac{\partial SV_4}{\partial TV_4} \quad (29)$$

where:

$$\Delta SV = SV_{closest} - SV_{measured} \text{ and } \Delta TV = TV_{closest} - TV_{solution} \quad (30)$$

$TV_{solution}$ is the refined vector of tissue values. The Jacobian matrix in the above set of equations can either be calculated when the TVSV data matrix is generated or it can be calculated at the time of the solution using adjacent values to the closest value in the TVSV matrix.

In this embodiment and others, the tissue oxygenation $StO_2$ can be calculated from the tissue values and displayed (e.g., on an oximetry device or an output screen) as:

$$StO_2 = \frac{C_{HbO2}}{c_{Hb} + c_{HbO2}} \quad (31)$$

In this embodiment and others, the total hemoglobin concentration can be calculated from the tissue values and displayed (e.g., on an oximetry device or an output screen) as:

$$THb = c_{Hb} + c_{HbO2} \quad (32)$$

The adipose layer thickness can be directly displayed from the corresponding tissue value.

The foregoing four-step algorithm can be used for measuring tissue oxygenation; however, other tissue parameters, such as sugar concentration, hydration, and other parameters can be determined if the requisite algorithm parameters are known or can be determined.

Figure 9:
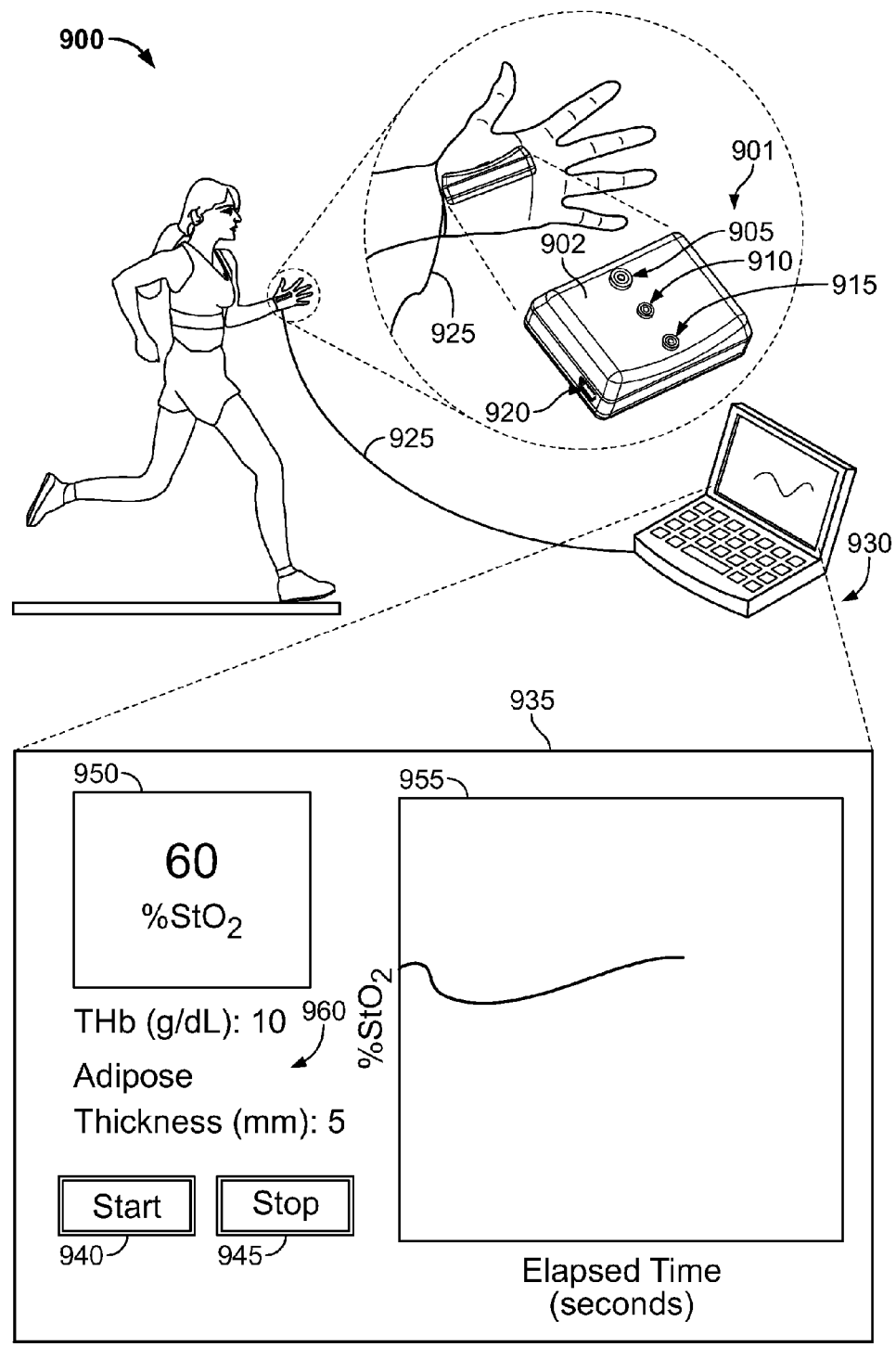
FIG. 9 illustrates a tissue oxygenation measurement system, according to one embodiment.

Referring now to FIG. 9, a tissue oxygenation measurement system (TOMS) 900 is shown according to one embodiment. For purposes of illustration, the TOMS 900 is shown in a configuration that provides for tissue oxygenation measurements on a person performing exercise (in this case, running on a treadmill). It will be understood in the following description of this and other embodiments, however, that alternative TOMS configurations can provide tissue oxygenation measurements in other areas on human and non-human subjects. In this and other embodiments, the TOMS 900 is capable of measuring hemoglobin oxygen saturation in arterial, venous, and microcirculation physiologies in various regions of the body, the results of which can be used by physicians or other practitioners for treating or diagnosing disease or studying physiological processes of the body, among other uses.

In this embodiment, the TOMS 900 includes a sensor device (hereinafter "sensor") 901 for obtaining remote tissue oxygenation measurements on a subject. The sensor 901 can be configured to be removably secured to a chosen location on the subject, such as the thenar eminence as illustrated in the blow-up region of the subject's hand in FIG. 9. In one example, the sensor 901 can be removably secured to the subject using a flexible, adhesive band configured to hold a front face 902 of the sensor 901 against the subject's skin.

In this embodiment, the front face 902 of the sensor 901 includes a light-projecting output window 905. In this embodiment, the window 905 is adjacent to the distal (output) end of a light-transmitting material such as a fiber optic cable or light pipe that is capable of propagating or transmitting light generated by one or more internally-housed light sources, e.g., light-emitting diodes (LEDs). In an exemplary embodiment, the light transmitting material is a length of optical-quality polycarbonate having a substantially polygonal cross-section, e.g., square, pentagonal, rectangular, triangular, octagonal, etc., with respect to the overall direction of light propagation, a length of about 6.5 mm, and a thickness of about 1.5 mm. The length of polycarbonate can be prepared according to methods known in the art for creating high-quality optical components with minimal optical loss over a desired wavelength range. In this exemplary embodiment, the sensor 901 includes four LEDs adjacently oriented so that their light output is optimally directed into the light-transmitting material, which may be, e.g., a polycarbonate light pipe having a square cross-section. As described herein, certain wavelengths of light can be used for interrogating selected material properties in tissue oxygenation measurements. Thus, while the foregoing examples describe the use of four LEDs for such purpose, it will be understood that fewer or additional LEDs, alone or in combination with one or more other types of light sources, can be used.

In this embodiment, the front face 902 of the sensor 901 includes first (910) and second (915) light-receiving windows. The first and second light-receiving windows 910, 915 are coupled to internally-housed light sensors, e.g., photodiodes that are configured to receive light (photons) that have propagated from the light-projecting window 905 through a selected tissue region of the subject. In general, a tissue region of interest can be selected according to the placement of the sensor 901 on the subject, and includes tissue substantially between the contact points of the light-projecting window 905 and the second light-receiving window 915 on the subject's skin. In general, tissue can be interrogated according to the methods described herein to a desired tissue depth (e.g., thickness) by controlling the spacing between the LEDs and the light-receiving windows, and other factors.

In this embodiment, the sensor 901 includes an input/output (I/O) port 920. The input/output port 920 provides for coupling to a source of electrical power to operate internal sensor 901 circuitry (described in greater detail herein), and also provides for bi-directional communication with a computing device 930 via a signal-transmitting cable 925. In this embodiment, the I/O port 920 is a universal serial bus (USB) port; however, various alternative circuit-powering and communication standards known in the art can be substituted according to preference or practical considerations. For example, the sensor 900 can be configured to utilize on-board battery power instead receiving power through the I/O port 920. In one exemplary embodiment, the sensor 901 can include the necessary circuitry, software, and peripheral components to enable bi-directional, wireless communication with the computing device 930, thereby eliminating the need for the cable 925. One non-limiting example of such an embodiment includes a sensor 901 having wireless communications components for sending and receiving signals, including data transmission, software code execution, and other signals, for communicating with a remote computing device 930 via a wireless protocol such as Bluetooth, IEEE 802 or the like.

In this embodiment, the computing device 930 is capable of executing stored software instructions that, when executed, cause the sensor 901 to carry out a locally-stored data-collection routine for the purpose of measuring tissue oxygenation in a selected tissue region of the subject, as described in greater detail herein. The computing device 930 is also capable of retrieving results of the data-collection routine, performing calculations for determining a selected tissue characteristic, such as % $StO_2$, which is described in greater detail herein, and displaying those data on a display device, such as a computer screen or monitor. Those skilled in the art will recognize the computing device 930 in FIG. 9 as a so-called "personal computer" (PC), which is capable of executing software code on various software operating platforms. In general, the computational methods described herein can be carried out on any suitable computing platform, e.g., personal computers, supercomputers, and the like.

In this embodiment, a software-driven user interface 935 for controlling the sensor 901 data-collection routine and displaying corresponding results is provided. The user interface 935 is displayed on the screen of the computing device 930 as illustrated by the blown-up region in FIG. 9. In this embodiment, the user interface 935 includes a start button 940 and a stop button 945 which, when an action such as a mouse click is performed thereon, causes the computing device 930 to send corresponding signal instructions to the sensor 901 to start or stop a data-collection routine, respectively. The computing device 930 can perform calculations of the type described herein to determine a tissue characteristic of interest, such as % StO2, from the collected data and display those results, along with other related data, if desired, in a variety of formats according to user preference. In this example, the user interface 935 indicates a measurement of 60% $StO_2$ in a latest-result text box 950, showing the most recent determination of the subject's tissue oxygenation in the selected region of interest. In this example, the user interface 935 also displays a moving chart of % $StO_2$ on the ordinate and time on the abscissa. In this example, the user interface also includes a text box 960 capable of displaying certain desired calculated or constant values corresponding to the measurement, such as total hemoglobin (THb) and adipose thickness, as shown.

In one embodiment, the computing device is capable of receiving signals, e.g., mouse clicks or keyboard input, that signifies the occurrence of certain events, such as a change in exercise routine, administration of a pharmaceutical compound or the like, donning an oxygen mask or spirometry device, etc. Receiving such a signal can cause a marker to be displayed on the screen and inserted into the collected tissue parameter data for later analysis.

In one embodiment, the computing device is capable of monitoring the calculated tissue parameter data, and sounding an alarm if the values are outside of certain pre-determined limits. In one example, an alarm can sound if the subject's % $StO_2$ falls below a certain safety threshold level.

In another embodiment (not shown), a user input control (e.g., keys, switches) mounted to the housing may be operable by the user to control data collection. In such examples, the user may be able to control when data collection occurs to permit, for example, rest breaks or interruptions in the exercise without an attendant operating the computing device 930.

In another embodiment, the run-time processing may be performed, and the results stored and sent for display on a display device that may be incorporated in the user interface 935.

Figure 10G:
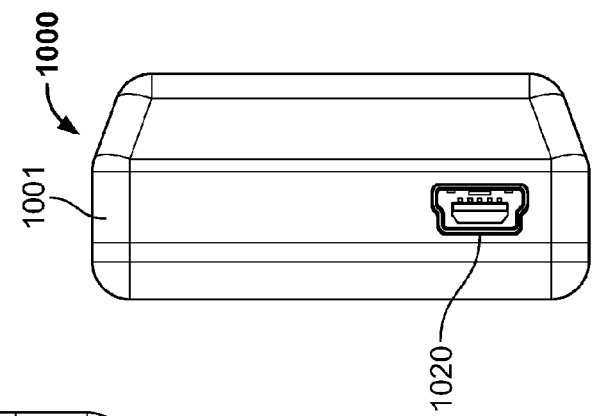
Figure 10E:
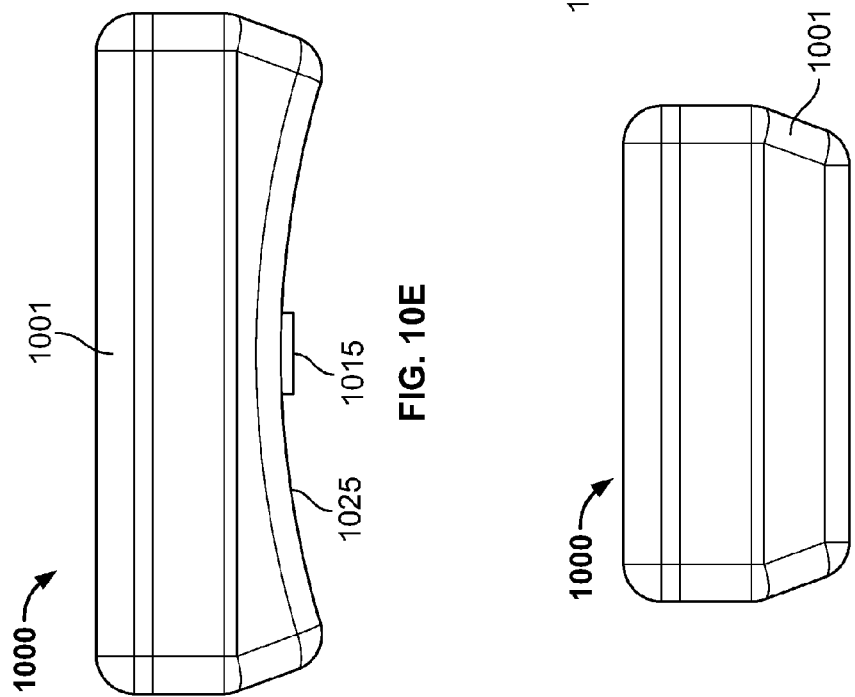
Figure 10F:
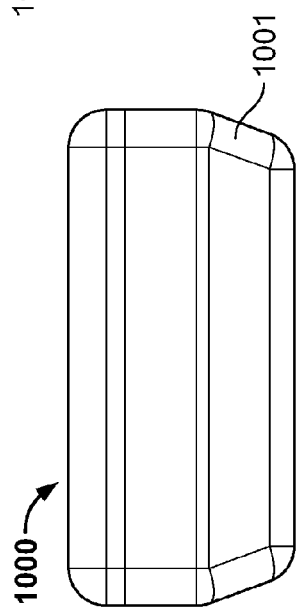
Figure 10D:
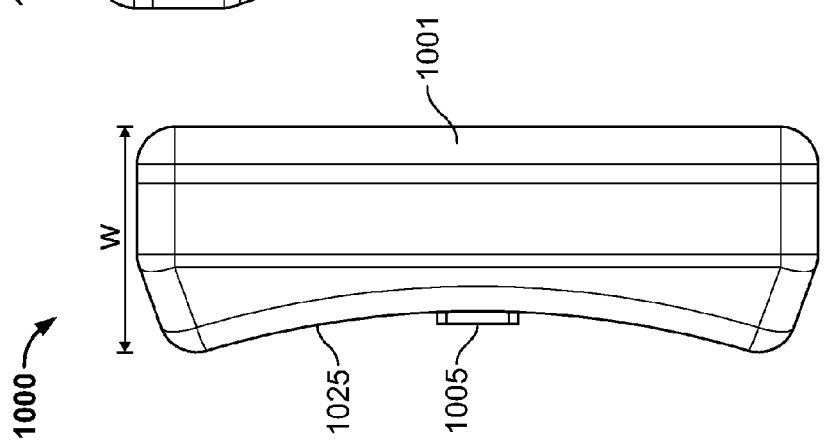
Figure 10H:
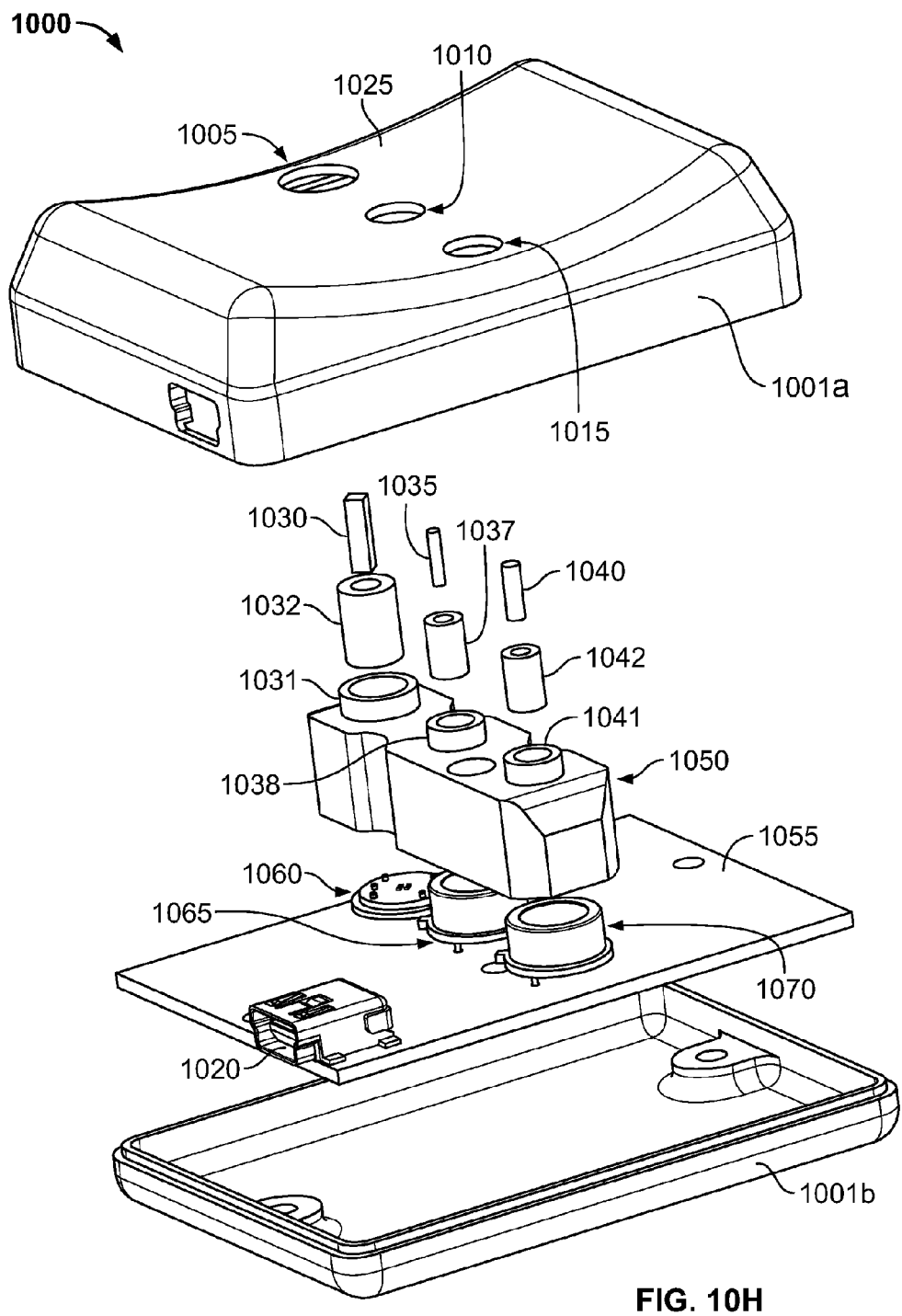

Referring now to FIGS. 10A-10H, a sensor 1000 is shown in various views, according to one embodiment. FIG. 10A is a perspective view of the sensor 1000; FIG. 10B is a front elevational view of the sensor 1000; FIG. 10C is a rear elevation view of the sensor 1000; FIG. 10D is a top-side elevational view of the sensor 1000; FIG. 10E is a bottom-side elevational view of the sensor 1000; FIG. 10F is a right-side elevational view of the sensor 1000; FIG. 10G is a left-side elevational view of the sensor 1000; and FIG. 10H is an exploded view of the sensor 1000, showing various internal components. The sensor 1000 can be of the type described herein, such as the sensor 901 described with respect to FIG. 9, and can be used in any embodiment described herein, including equivalent and alternative embodiments.

In this embodiment, the sensor 1000 includes a housing 1001 which can be made of a lightweight, durable material such as plastic, although other suitable materials can be used. The sensor 1000 includes the elements of the sensor 901 described with respect to FIG. 9, e.g., a light-projecting output window 1005, a first light-receiving window 1010, a second light-receiving window 1015, and a USB I/O port 1020. Referring specifically to FIG. 10B, the light-projecting output window 1005, and the first (1010) and second (1015) light-receiving windows are arranged substantially collinearly, as illustrated, although configurations other than collinear can be used. For example, the light-receiving windows and the light-projecting window can be arranged in a triangle. The spacing between these optical elements can be chosen according to user preference and to optimize signal capture during data collection. In one illustrative example, the distance $d_s$ between the geometric centers of the light-projecting output window 1005 and the first light-receiving window 1010 can be positioned at the midpoint of the distance $d_l$ between the first light-receiving window 1010 and the second light-receiving window 1015, as illustrated, for purposes described herein.

In this and other embodiments, the light source(s) e.g., the LEDs 1060 can be arranged substantially adjacently, so that their light output is optimally coupled to the light-transmitting material, e.g., a square, polycarbonate light pipe. Other optical components such as lenses and the like can be used for optimal light output coupling between the light source(s) and the light-transmitting medium.

In this embodiment, the front face of the housing 1001 has a concave surface contour defined by an arcuate wall member 1025 as illustrated. The contour of the wall member 1025 can be advantageously selected to provide complementary mating with a chosen physiology of the subject. In this example, the contour of the wall member 1025 is optimized so as to provide matching engagement with the gastrocnemius muscle of the lower leg. It will be understood that in other embodiments, the front face of the housing 1010 can be configured in any shape to optimize mating engagement of the sensor 1000 with selected subject physiology.

Referring specifically to FIG. 10H, internal components of the sensor 1000 are shown in an exploded view, according to one embodiment. In this embodiment, the housing (1000) includes a top clamshell half 1001a and a bottom clamshell half 1001b that can be engaged to encapsulate and protect the internal components in an operational configuration as shown in FIG. 10A.

In this embodiment, the sensor 1000 includes a circuit board 1055 that provides signal communication and any necessary electrical power between an LED driver module 1060, two photodiode modules 1065, 1070, respectively, the I/O port 1020, and any other electronic components used by the sensor for collecting sensor value data as described herein. (See, e.g., FIG. 11 and related description for other electronic components that can be included in the sensor 1000.)

In this embodiment, the LED driver module 1060 can include one or more LEDs which, in some embodiments, can produce different spectral light output at a selected intensity or power.

In this embodiment, a housing 1050 is configured to isolate the output of the LEDs 1060 from the photodiodes 1065, 1070 (e.g., so that the photodiodes do not pick up LED light output directly from the LED). The housing 1050 can be sealingly engaged with the circuit board 1055 in an assembled sensor configuration, e.g., the configuration shown in FIG. 10A. With respect to the LED module 1060, the housing is configured to allow light to project through a bore defined by a cylindrically-shaped wall member 1031 which houses a cylindrically-shaped coupling member 1032 having a bore therethrough as illustrated. The coupling member 1032 is configured to engage a light-transmitting material 1030, e.g., a rectangular light pipe composed of polycarbonate.

Similarly, with respect to the photodiodes 1065, 1070, the housing 1050 is configured to allow light to be received independently from the light receiving windows 1010, 1015, respectively, onto the photodiodes 1065, 1070. A cylindrically-shaped coupling member 1037 (1042) houses a fiber optic 1035 (1040) which transmits light received through the windows 1010, 1015 to the photodiodes 1065 (1070). A bore defined by a cylindrically-shaped wall member 1038 (1041) houses the coupling member 1037 (1042) when the sensor is in an operative configuration.

Figure 11:
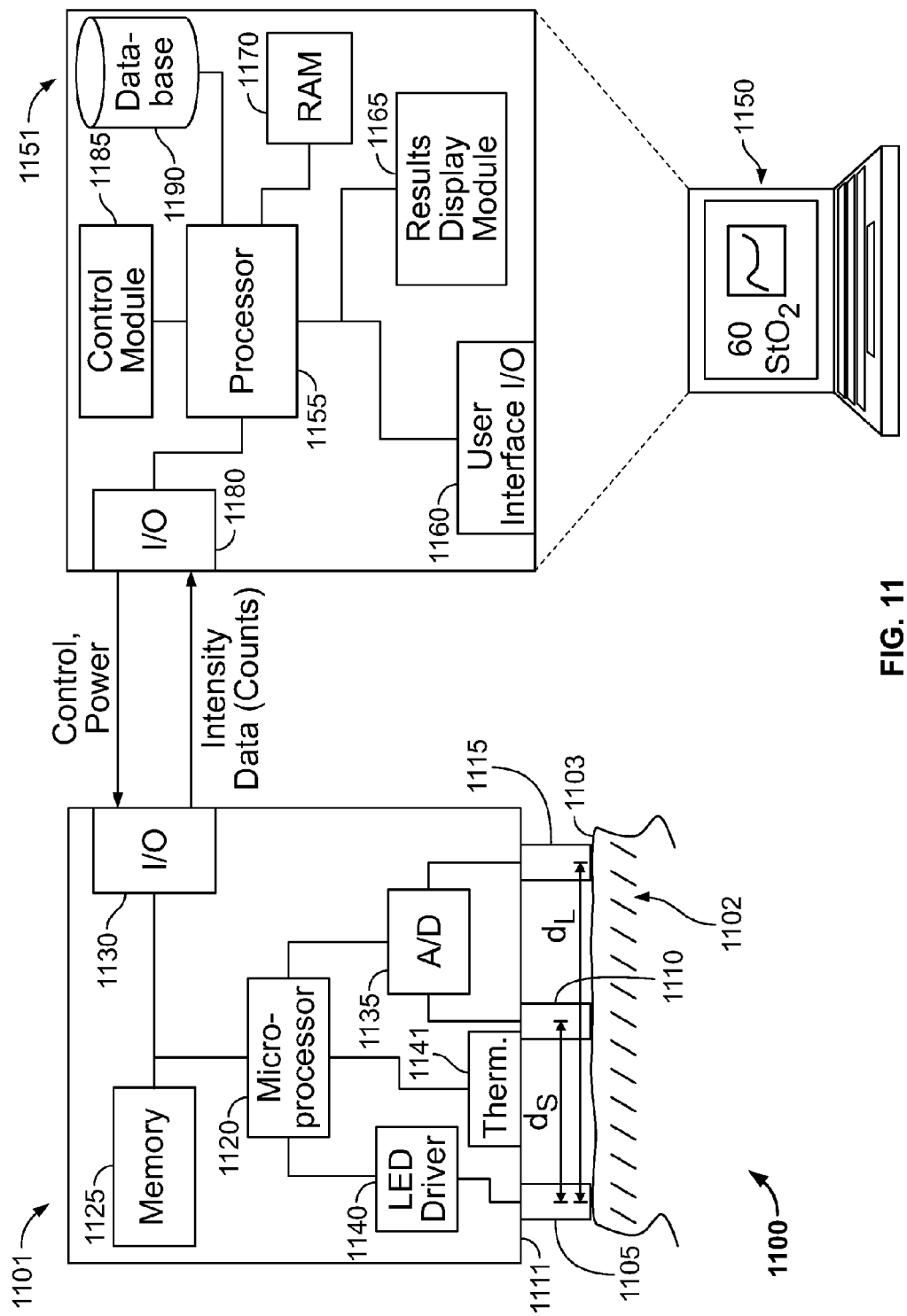
FIG. 11 is an illustration of a computer-implemented tissue oxygenation measurement system, according to one embodiment.

Referring now to FIG. 11, a computer-implemented tissue oxygenation measurement system (hereinafter "system") 1100 is shown according to one embodiment. In this embodiment, the system 1100 includes a sensor 1101 having a front face 1111 configured to be brought into confronting relationship with the surface 1103 of a selected region of tissue 1102. In this embodiment, the sensor 1101 can be a sensor as described herein, such as the sensor described with respect to FIGS. 9 and 10A-10H, and can include elements thereof not illustrated in the sensor 1101 of FIG. 11. For purposes of this illustration, the selected region of tissue 1102 in FIG. 11 is the thenar eminence of the hand, although other tissue regions can be selected.

In this embodiment, the sensor 1101 includes a light-projecting output window 1105 and first (1110) and second (1115) light-receiving windows arranged as depicted in the sensor 1000 embodiment of FIGS. 10A-10H. The distance $d_s$ between the light-projecting output window 1105 and the first light-receiving window 1110 is substantially one-half the distance $d_l$ between the light-projecting output window 1105 and the second light-receiving window 1115.

In this embodiment, the sensor 1101 includes an internally-housed electronic circuitry and components that enable tissue oxygenation sampling measurements as described herein. While the described circuitry and arrangement of components provides requisite functionality for the present embodiment, it will be understood that other arrangements and substitution of components can be used in other embodiments.

In this embodiment, the sensor 1101 includes a microprocessor 1120 that is capable of executing stored software commands as well as commands received by other electronic components. The microprocessor 1120 is in data communication with a memory module 1125 that is capable of storing software instructions and measurement data when the sensor 1101 is operational. In this embodiment, the memory 1125 is random-access memory (RAM); however, other memory types can be used, such as ROM, or physical storage devices such as flash drives or hard-disk drives, which will be apparent to those skilled in the art.

In this embodiment, the sensor 1101 includes an I/O port 1130 for sending and receiving signal information to/from a control computer 1150. Signal information can include control signals, e.g., signals that initialize a data-collection routine on the sensor 1101 or signals that request or send measurement data from the sensor 1101. The I/O port 1130 can also be used to provide requisite power for the sensor circuitry and peripheral components, such as by transmitting power through a USB connection between the sensor 1101 and the control computer 1150.

In this embodiment, the sensor 1101 includes an LED driver module 1140 that is capable of individually controlling the light output of one or more LEDs according to a predetermined illumination sequence. In this embodiment, four LEDs are used, and the light output is optically coupled to the light-projecting output window via a light-transmitting material such as a fiber optic or the previously-described length of polycarbonate material. In this and other embodiments, the LEDs (in this case, four LEDs) can be adjacently arranged so that light output coupling into the light-transmitting material is optimized, e.g., any optical loss is minimized. The LED driver module 1140 can activate (e.g., turn on) the LEDs individually using a predetermined driving power, or, in some embodiments, collectively, for a pre-determined integration cycle time period, and subsequently de-activate (e.g., turn off) the LED(s).

In general, the predetermined illumination sequence can be stored as part of an overall data-collection routine that can be stored, e.g., in the memory 1125 of the sensor 1101. The illumination sequence and integration cycle (the length of time that the LED is turned on) can be chosen according to user preference and is described in greater detail herein. In this embodiment, the LED driver module 1140 is capable of at least performing the illumination sequence: LED1-on; LED1-off; LED2-on; LED2-off; LED3-on; LED3-off; LED4-on; LED4-off; wherein the length of "on" or "off" time can be set according to user preference. In an exemplary embodiment, the LED driver module is a model ADG812 Quad Single Pole Single Throw Switch produced by Analog Devices, Inc. of Massachusetts.

In this embodiment, the sensor 1101 includes an LED temperature-measuring device (temperature sensor 1141). The temperature sensor 1141 can be placed on or near the LED array for the purpose of collecting an average temperature measurement of the LEDs. In an exemplary embodiment, the temperature sensor is a BD1020HFV temperature sensor produced by Rohm Semiconductor, Inc. of Japan.

In this embodiment, the sensor 1101 includes an analog-to-digital (A/D) converter 1135. The A/D converter 1135 is in signal communication with two photodiodes (not illustrated in FIG. 11 for clarity), each of which is configured to receive light that passes through the light-receiving window. In general, the photodiodes are configured to receive light that propagates from the light-projecting output window 1105, through the tissue region 1102, to the first (1110) and second (1115) light-receiving windows, respectively, as illustrated.

In this embodiment, the photodiodes are those provided by Hamamatsu, of Japan, Model No. S1226-5BK, however, suitable alternatives can be used. In this embodiment, the A/D converter converts an analog signal corresponding to the current of the photodiode resulting from light impingement thereon into a digital signal that can be used to determine "counts"—a representative value corresponding to the number of photons that struck the photodiode during the integration cycle.

In this and other embodiments, each component of the sensor 1101 can be in signal communication with other components either directly or via the microprocessor 1120. For example, the microprocessor 1120 can load a data collection routine from the memory module 1125; the microprocessor 1120 can then execute the instructions of the data collection routine to generate activation signals to the LED driver 1140, which causes controlled illumination of the LEDs (individually or collectively). Concurrently, the A/D converter 1135 can send count information to the microprocessor 1120 during an integration cycle; these data can be sent to the memory module 1125—which can include temporary memory storage such as a memory buffer. The count data can be sent to the I/O port by the microprocessor 1120 automatically, or upon request by the control computer 1150.

In this embodiment, the control computer 1150 includes hardware, software, and peripheral devices such as display devices, communications ports, and other elements commonly found in commercially-available computing devices. In this embodiment, the control computer 1150 includes a control system 1151 for sending data-collection control commands to the sensor 1101, receiving data therefrom, calculating measurement results, and managing the data for storage, display, or any other desired purpose.

In this embodiment, the control system 1151 includes a processor 1155, which can be a central processing unit (CPU) found in commercially-available personal computers. The processor 1155 is in signal communication with, and provides electronic control or instructions to several modules: a user interface module 1160; a results display module 1165; a memory module (RAM 1170), an I/O port 1180, a control module 1185, and a database 1190. It will be understood that other, peripheral computer components may be necessary to operate the control system 1151 which are not shown in FIG. 11 for the purpose of clarity.

In this embodiment, the control module 1185 can include software instructions for executing a sensor data collection sequence, receiving data from the sensor 1101, performing calculations and other functions on the data, using the data to determine one or more desired tissue parameters, and providing user-readable output that includes the one or more desired tissue parameters. Detailed descriptions of such processes are described herein.

In this embodiment, the user interface I/O 1160 module can provide a graphical user interface, where the user can control the starting or stopping of a data collection routine, input any constants or other variables into the system, or perform other functions relating to tissue measurements such as determining % $StO_2$. In this embodiment, the user interface I/O module 1160 provides the functionality for the user to input commands into the system 1151 and includes, e.g., necessary software and hardware components to receive input from keyboards, peripheral pointing devices such as mice and the like, and any other desired interface components.

In this embodiment, the I/O port 1180 can be a USB or other communications port capable of communicating with the sensor 1101 to send and receive commands and data, respectively, as described. For example, during the execution of a tissue oxygenation measurement routine, the control module 1185 can send an instruction via the processor 1155 to receive measurement data from the sensor 1101. This instruction can open the I/O port 1180, allowing sensor measurement data to be received by the system 1151.

In this embodiment, the database 1190 can store look-up tables containing calculated tissue oxygenation levels and other parameters, which the control module 1185 can use to determine tissue oxygenation levels of the subject, as measured by the sensor 1101. This process is described in greater detail herein.

In this embodiment, the RAM module 1170 can be used for general purpose caching and temporary storage of data, including data relating to tissue oxygenation measurements, and also any general data or functions required to manage the operation of the control system 1151 or the operating platform of the computer 1150.

In this embodiment, a results display module 1165 can be used for displaying the results of tissue oxygenation measurements in cooperation with the user interface I/O module 1160. The results display module 1165 can include, e.g., drivers, software (including third-party software), and other computer-implemented components that provide the ability to visualize data, charts and graphs, and other computer-generated information.

The following example describes the operation of the system 1100 for the purpose of collecting a tissue oxygenation measurement, according to one embodiment.

First, a user can attach the sensor 1101 to a selected region of the subject's skin surface 1103 (such as the thenar eminence of the hand) in an orientation that allows light from the light-projecting output window 1105 to shine substantially normal to the surface 1103, and into the tissue region of interest 1102.

Next, the user can load a tissue oxygenation software program stored in memory 1125 and which is executed by the control module 1185; using the GUI of the program, the user can enter certain constants, tissue parameters, user or subject information, or other pertinent information used by the control module 1185 during execution of the program via the user interface I/O 1160. The user can activate the measurement process by, e.g., clicking on a start button (such as that shown in FIG. 9) of the GUI. Next, the processor can send an initialization command to the sensor 1101 via the I/O 1180, which can be received by the sensor I/O 1130. Upon receiving the initialization command, the sensor microprocessor 1120 can execute a sequence of locally-stored data-collection commands from the memory module 1125.

In this example, the data-collection commands include instructions for activating a first LED, which command is sent to the LED driver 1140, and the first LED is turned on for a predetermined length of time. The next or concurrent command is to read the intensity value provided by the A/D converter 1135 for each of the two photodiodes in the sensor 1101 for a predetermined integration cycle. These data are stored in the memory buffer (1125), along with a temperature reading from the temperature sensor 1141. The next command is to deactivate all LEDs for a predetermined period, and subsequently or concurrently read the intensity values of the photodiodes provided by the A/D converter 1135 again (this is the all-dark reading). The next command is to activate the second LED only, read the intensity values of the photodiodes in the same manner, deactivate all LEDs, and capture the all-dark reading of the photodiodes. These data are similarly stored in the memory buffer 1125 as previously described. This process repeats for the third and fourth LEDs, so that photodiode intensity data is iteratively collected according to the overall sequence: LED1-on; all dark; LED2-on; all dark; LED3-on; all dark; LED4-on; all dark. A temperature reading can be collected with each photodiode reading during each LED activation cycle.

The photodiode and temperature readings can be streamed to the sensor I/O port 1130, in real-time, so that when the control system 1151 sends a request for sensor value data, the photodiode and temperature readings are immediately available. Next, as the control system 1151 receives sensor data, the control module 1185 accesses a pertinent look-up table in the database 1190. The control module 1185 can calculate the % $StO_2$ of the subject according to the methods described herein. Those results can be sent to the results display module 1165, where they can be formatted into charts, graphs, or other displays of pertinent information, and subsequently sent to the user interface I/O for display on a computer screen or other display device.

Figure 12:
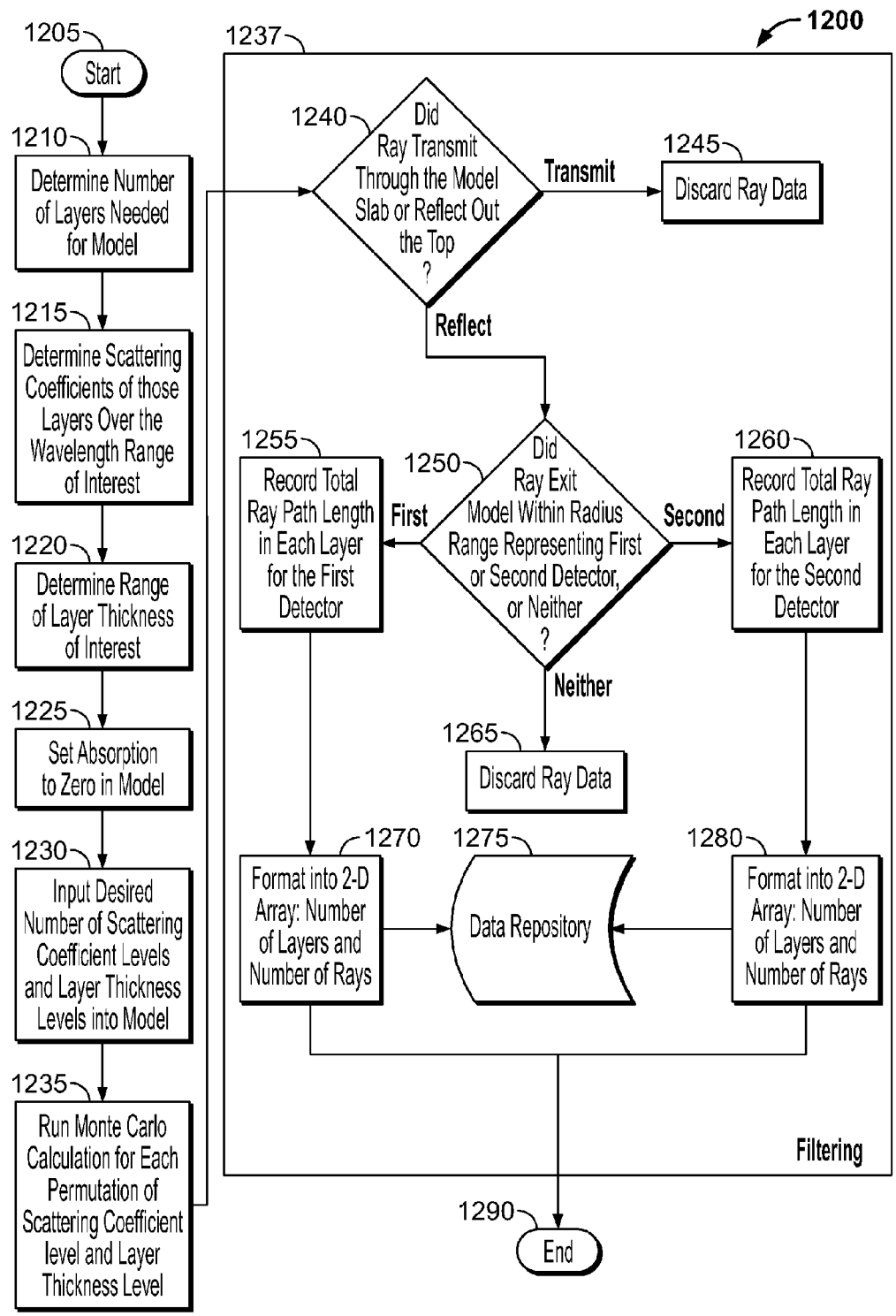
FIG. 12 shows a process for generating a look-up table that includes calculated % $StO_2$ values for a tissue region of interest, according to one embodiment.

Referring now to FIG. 12, a computer-implemented process 1200 is shown that illustrates the design-time steps of generating a look-up table that includes calculated % $StO_2$ values for a tissue region of interest, according to one embodiment. The generated look-up table can be used for the purpose of determining % $StO_2$ in a selected tissue region of interest from measured sensor values according to any of the embodiments described herein. In general, the sequence 1200 outlines the steps of modeling the tissue of interest, and predicting % $StO_2$ values based on light absorbance using Monte Carlo methods.

The sequence 1200 begins at step 1205. At step 1210, the tissue region of interest, e.g., the tissue that will be measured using a sensor of the type described herein is contemplated, and the number of layers needed to accurately model the tissue is determined. The number of layers required for the model can be determined by the user according to the physiology of the tissue region of interest. For example, a model can be constructed using a four-layer tissue sample including epidermis, dermis, adipose, and muscle tissue.

Next, at step 1215, the scattering coefficients of the individual layers are determined over the wavelength range of interest. The scattering coefficients can be referenced in various journals or reference volumes; one exemplary reference volume is Tissue Optics, Second Edition, Valery Tuchin, SPIE Press, 2007. The wavelength range of interest can be selected by the user and generally contemplates the absorption properties of the target analyte (e.g., oxyhemoglobin) as well as the surrounding tissue.

Next, at step 1220, the range of layer thicknesses of the tissue are determined. In general, the thickness of the epidermis and dermis layers in human subjects is fairly consistent; however, adipose layers can vary greatly from person-to-person. In one approach, the range of layer thicknesses can be from about 1 mm to about 20 mm, which accounts for variation in adipose layer thickness.

Next, at step 1225, the tissue absorption coefficient in the model is set to zero.

Next, at step 1230, the desired number of scattering coefficient levels and the desired number of layer thickness levels are entered into the model in the form of a two-dimensional matrix with scattering in one dimension and layer thickness in the other dimension. For example, the model can be set up with 15 scattering levels and 12 layer thickness levels.

Next, at step 1235, a Monte Carlo calculation is performed for each permutation of scattering coefficient level and layer thickness level. In keeping with the above example, 180 Monte Carlo calculations would be performed for the model with 15 scattering levels and 12 layer thickness levels.

The following steps in the sequence 1200 can be generally categorized as a filtering process (as outlined by the box 1237 in FIG. 12) for the calculated Monte Carlo data produced in step 1235.

The filtering process considers the theoretical framework of the model, which, in this example, is the problem of an infinite slab of finite thickness. In this embodiment, the results of the Monte Carlo calculations are filtered based on two factors. The first factor considers whether a ray, after being launched into the model, is transmitted through the model slab, or reflected out the top (decision point 1240). If the ray transmitted through the slab, that data is discarded (step 1245). If, however, the ray reflected out the top of the model, a second factor is considered. The second factor considers the location that the ray exited the model in relation to the modeled detector location; the results can be filtered, e.g., based on a radius range from the injection point of the ray. For example, an acceptable radius range for the modeled distal detector (e.g., light-receiving window 1015 in FIG. 10A) may be defined as a radius between 24.25 mm and 25.75 mm, where the detector is assumed to be 25.00 mm from the injection point (denoted $d_I$ in FIG. 10B). This approach thus defines a 1.5 mm thick "ring" of acceptable ray exit locations in the model, whose geometric center (origin of the radius) is at the ray origin. Decision point 1250 determines whether the ray exited the model within the acceptable radius range defined for the first and second detectors or neither. In the latter case, the ray data is discarded.

Next, if the ray exited the model within the acceptable ranges defined for the first or second detector respectively, the total ray path length in each layer of the model is recorded for the first detector (step 1255) and the second detector (step 1260).

The output of steps 1255 and 1260 is a list of rays and their path lengths in each layer. Steps 1270 and 1280 format the lists into 2D arrays where one dimension includes the modeled layers and the other dimension includes the number of rays from the output of steps 1255 and 1260. The 2D arrays are stored in a data repository such as a database, at step 1275. The process ends at process point 1290.

Figure 13:
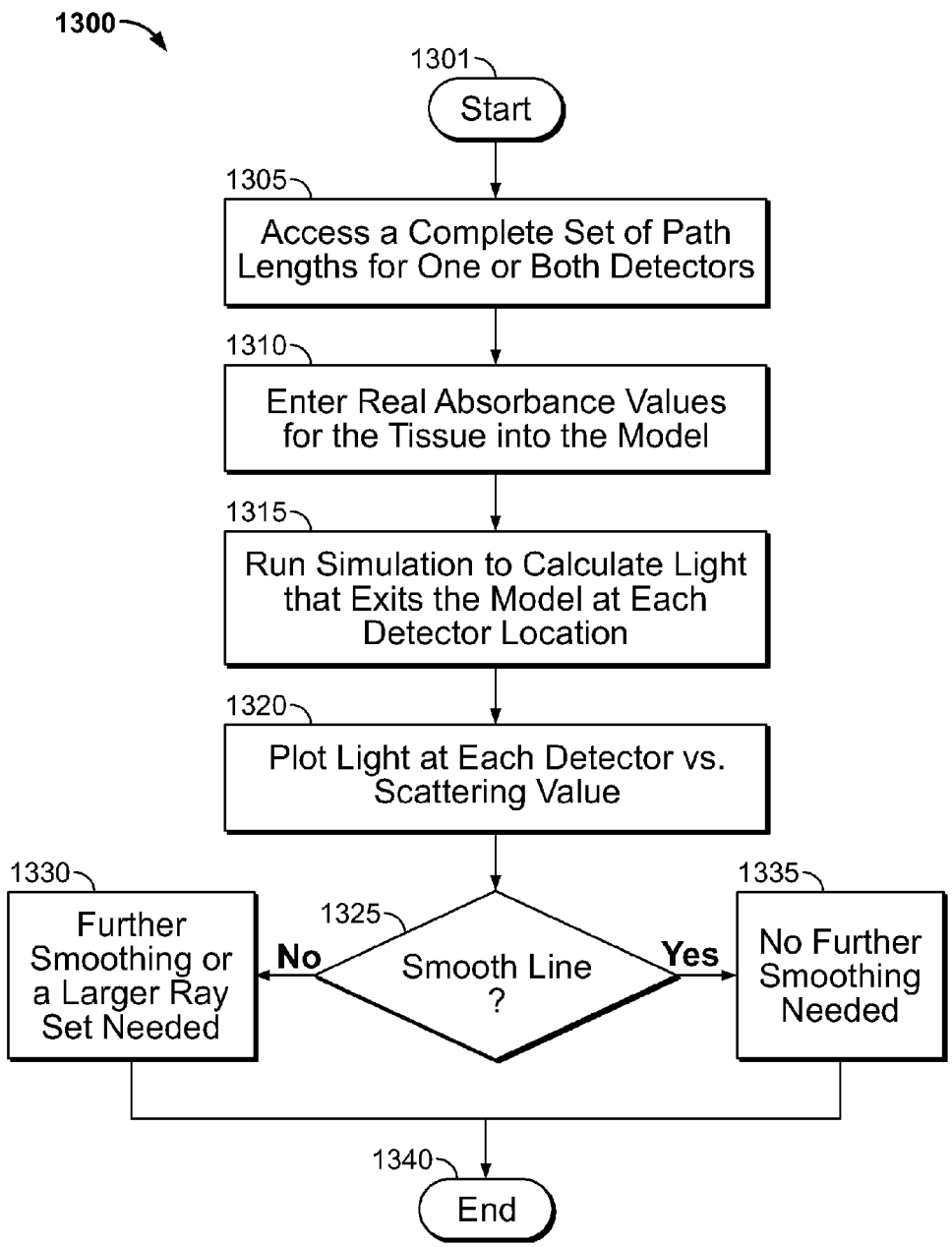
FIG. 13 shows a process for determining smoothness, according to one embodiment.

Referring now to FIG. 13, a computer-implemented process 1300 is shown for determining if the data in the look-up table generated by the above process is smooth enough, with respect to scattering, so as to provide reliable results when comparing measured data to the look-up table data. In other words, the test determines if there are enough rays in the Monte Carlo run to produce a result that is representative of actual tissue.

The process begins at process point 1301. Next, at step 1305, a complete set of path lengths for one or both detectors is selected from the look-up table generated from the process described in FIG. 12.

Next, at step 1310, a real absorbance value (based on real tissue values) is entered into the model with selected tissue parameters, e.g., 50% $StO_2$, a hemoglobin content of 4 g/L and an adipose layer thickness of 5 mm.

Next, at step 1315, a simulation is performed on the model to calculate the intensity of light that exits the model at each detector location.

Next, at step 1320, the light is plotted at each detector versus the scattering value used in the model. If the plot reveals a smooth line (decision 1325), further smoothing of the data may not be needed (step 1335); however, if the plot reveals a jagged or otherwise un-smooth line, further smoothing of the data may be needed (step 1330). The process ends at process point 1340. In this embodiment, the determination of smoothness can be considered as having residuals less than a certain percentage of the value predicted by a low order polynomial fit to the data. For example, residuals of less than 5% of the value predicted by a 2nd order polynomial fit; however, other approaches can be used.

Figure 14:
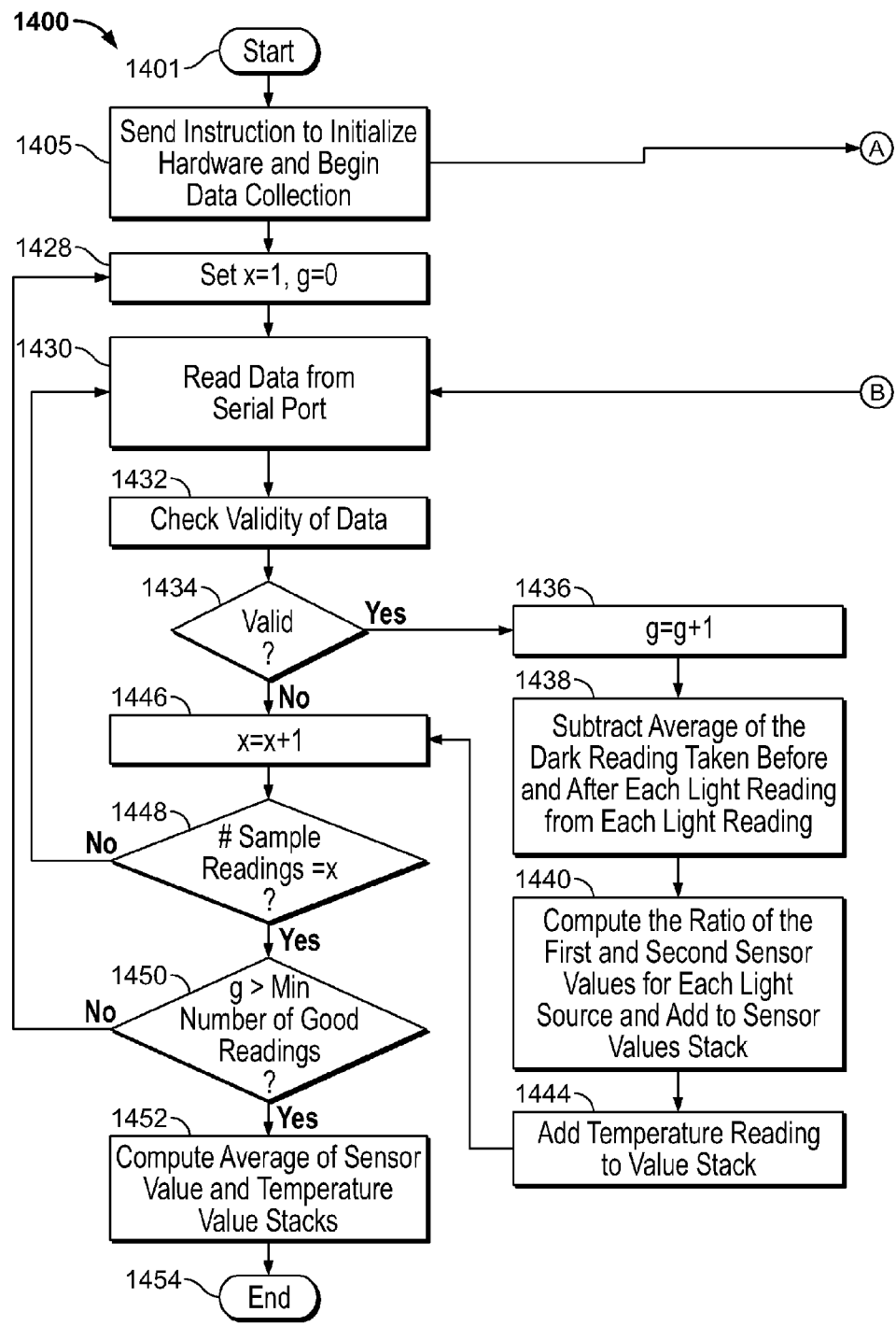
FIG. 14 shows a process for collecting tissue measurements from a remote sensor, according to one embodiment.
Figure 14:
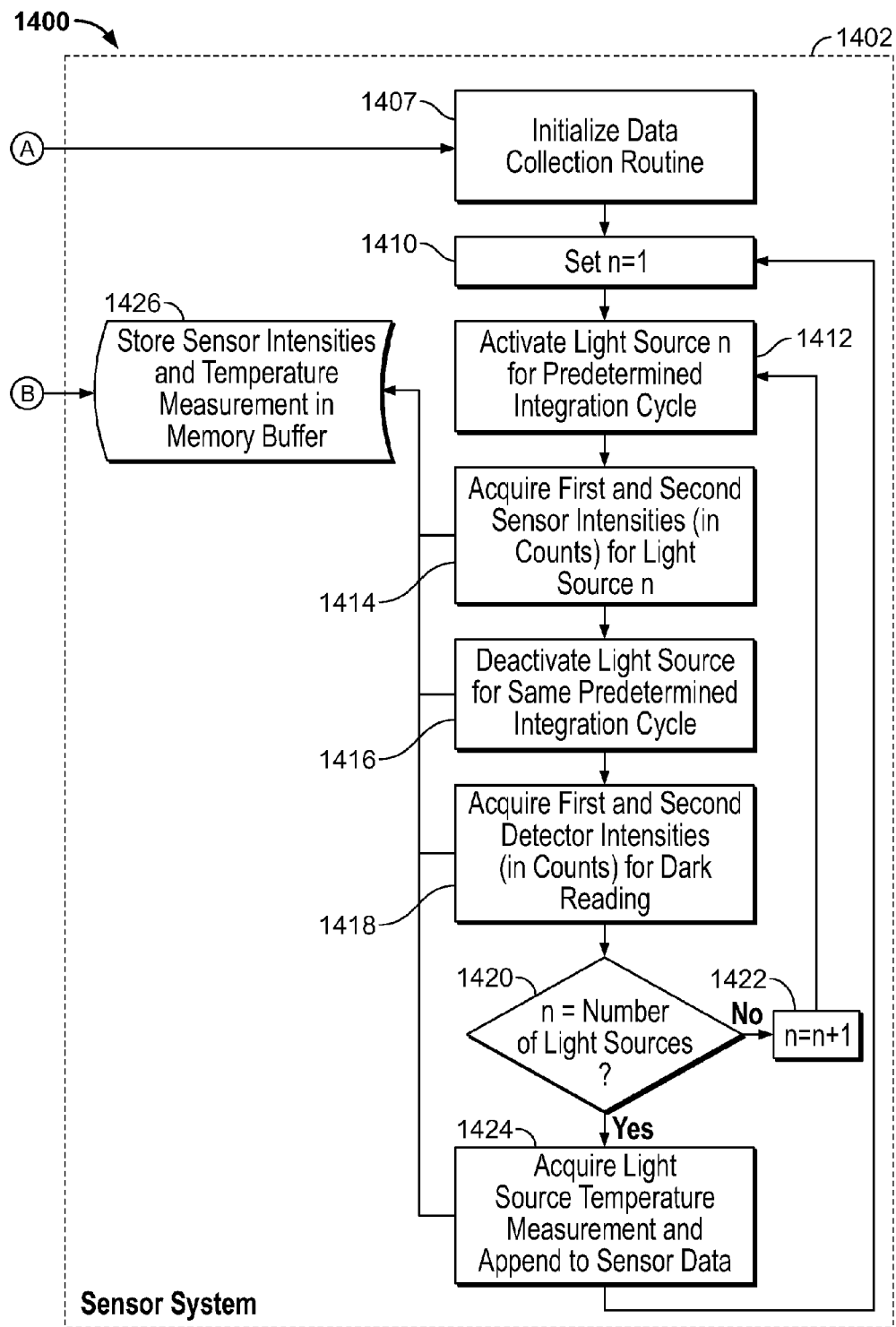

Referring now to FIG. 14, a computer-implemented process for collecting sensor value data 1400 is illustrated by way of the flowchart, according to one embodiment. The process 1400 is described here for collecting sensor value data for determining % $StO_2$, however, it will be understood that this process can be extended or modified for interrogating other analytes in tissue. The following description makes reference to the components of the tissue oxygenation measurement system 1100 described with respect to FIG. 11 for illustrative purposes, however it will be understood the process 1400 can be extended to other systems as well. The steps contained within the dashed line 1402 of the process 1400 indicate steps carried out by the sensor circuitry.

The process 1400 begins at process point 1401. At step 1405, as part of a request for sensor data, the control system 1151 sends an initialization command to the sensor 1101, which is received by the sensor microprocessor 1120.

Next, at step 1407, the sensor microprocessor 1120 can initialize a stored data collection routine. For example, the various circuitry components can be powered up, any configuration or data execution files can be loaded, or configuration checks can be executed.

Step 1410 defines the beginning of a loop by setting n=1, where n represents the total number of LEDs used by the sensor for collecting tissue data. In an exemplary sensor configuration, n=4.

Next, at step 1412, the nth light source is activated via the LED driver 1140 for a period of time equal to a pre-established integration cycle. In this and other embodiments, each LED can be capable of outputting light at a chosen center wavelength. In an exemplary sensor configuration, n=4, and the LEDs are capable of individually outputting light having center wavelengths at about 680 nm, about 720 nm, about 760 nm, and about 800 nm, respectively.

Next, at step 1414, the microprocessor 1120 reads the A/D converter 1135 to acquire intensity measurements (counts) from the first (1110) and second (1115) photodiodes.

Next, at step 1416, the nth LED is turned off for the same pre-established integration cycle time period as the "on" cycle time period to collect a "dark count" measurement from the photodiode.

Next, at step 1418, the microprocessor 1120 reads the A/D converter 1135 to acquire a dark count measurement from the first (1110) and second (1115) photodiodes.

Decision point 1420 determines if the number of loop iterations beginning with step 1412 is equal to n, the number of photodiodes present in the sensor. If not, n is incremented to n=n+1, and the process is directed to step 1412 to collect photodiode count measurements using the next LED as the light source. This process continues until photodiode count measurements have been collected for each LED, i.e., for each desired wavelength.

Next, at step 1424, an LED temperature measurement is obtained at the thermocouple 1141; this information is added to the photodiode count values collected in steps 1412-1418.

The photodiode count measurements for each wavelength plus the temperature measurement are stored in a memory buffer 1125 of the sensor 1101 (step 1426), and the data collection process on the sensor 1101 begins again by returning to step 1410. During operation, in one embodiment, the sensor can continually gather sensor values in the manner described. The sensor values (and temperature) can remain in the memory buffer 1125 until a call is made by the control system 1151 for the data. In this and other embodiments, the I/O port 1130 can cooperate with the on-board memory 1125 to ensure data integrity, including providing data to the control system 1151 only if it meets certain criteria, e.g., including a line-feed character at the end of the data set or an alternative identifier that the data set is complete.

Next, on the control system side at step 1428, a first counter value x is set to 1, and a second counter value g is set to 0 (zero). In this embodiment, the desired number of sample readings to be obtained can be set in the control module 1185 program options, e.g., 25 readings. In order to provide a constant update rate of % $StO_2$ readings, a threshold level of acceptable readings (described below) can be set in the control module 1185 program options. If the number of acceptable readings is equal to, or greater than this threshold value, the readings can be used for calculating % $StO_2$; otherwise the data can be discarded and a non-numerical character such as "--" can be displayed. In this embodiment, the minimum number of acceptable readings is 3, however, other values can be used.

Next, at step 1430, the control module 1185 requests the stored sensor value data from the memory buffer 1125 of the sensor 1101. The data can be sent via the I/O port 1130 of the sensor 1101 and received by the I/O port of the control system 1151.

Next, at step 1432, the validity of the received sensor value data is checked. "Valid" data can be data that meets certain threshold criteria to ensure that the sensor 1101 is performing within expected parameters and that data integrity is maintained as it is transferred from the sensor 1101 to the control system 1151. Exemplary data validity checks include, but are not limited to: ensuring the A/D converter is not saturated (which may be evidenced by a string of readings with excessive count values); ensuring that the dark counts remain stable between readings; and other validity checks.

Next, at decision point 1434, if the sensor readings do not fall within the normal operating parameters, the data are rejected and the process continues to step 1446, where x is incremented by 1; if the number of sample readings is less than x (decision point 1448), the process loops back to step 1430 to collect additional sensor values.

Referring back to decision point 1434, if the data are valid the process continues to step 1436, where g is incremented by one (1). Next, at step 1438, the average of the dark readings taken prior to, and subsequent each light reading are subtracted from each light reading. This process is similar to subtracting a constant background signal and results readings that are substantially baseline corrected. Referring back to step 1412, the first step in collecting photodiode counts when the sensor is initialized is to collect the light counts for LED1, when n=1. In this case, since there is no preceding dark count measurement to subtract in step 1438, the control system may disregard the first sensor reading, with the exception of the last dark count reading, and use this reading on the subsequent cycle in step 1438.

Next, at step 1440, the ratio of the first and second sensor values is computed for each LED, e.g., for n=1, 2, 3, 4, and this ratio is added to the sensor values stack, i.e., the sensor values retrieved from the memory buffer (step 1430). Next, at step 1444, the temperature value measured in step 1424 are added to a stack for later averaging.

Next, at step 1446, x is incremented by one (1) as previously described; if the value of x is equal to the number of desired sample readings (decision point 1448) the process continues to process point 1450. Here, the control system 1151 determines if, for the entire set of collected sample readings, the number of good readings g is greater than the minimum threshold set in the control program options, as previously described. If not, the process loops back to step 1428 to start over again, and the control system can disregard the data. In such cases, the disregarded data point (as seen by the user) can be indicated by a non-value character as previously described.

Next, at step 1452, if g is greater than the number of threshold good readings required, the average of the sensor value stacks, and the average of the temperature value stacks are calculated. This result represents the sensor data used in determining % $StO_2$ values from a look-up table as described in the following process (the TVSV matrix, as described above). The process ends at process point 1454.

Figure 15:
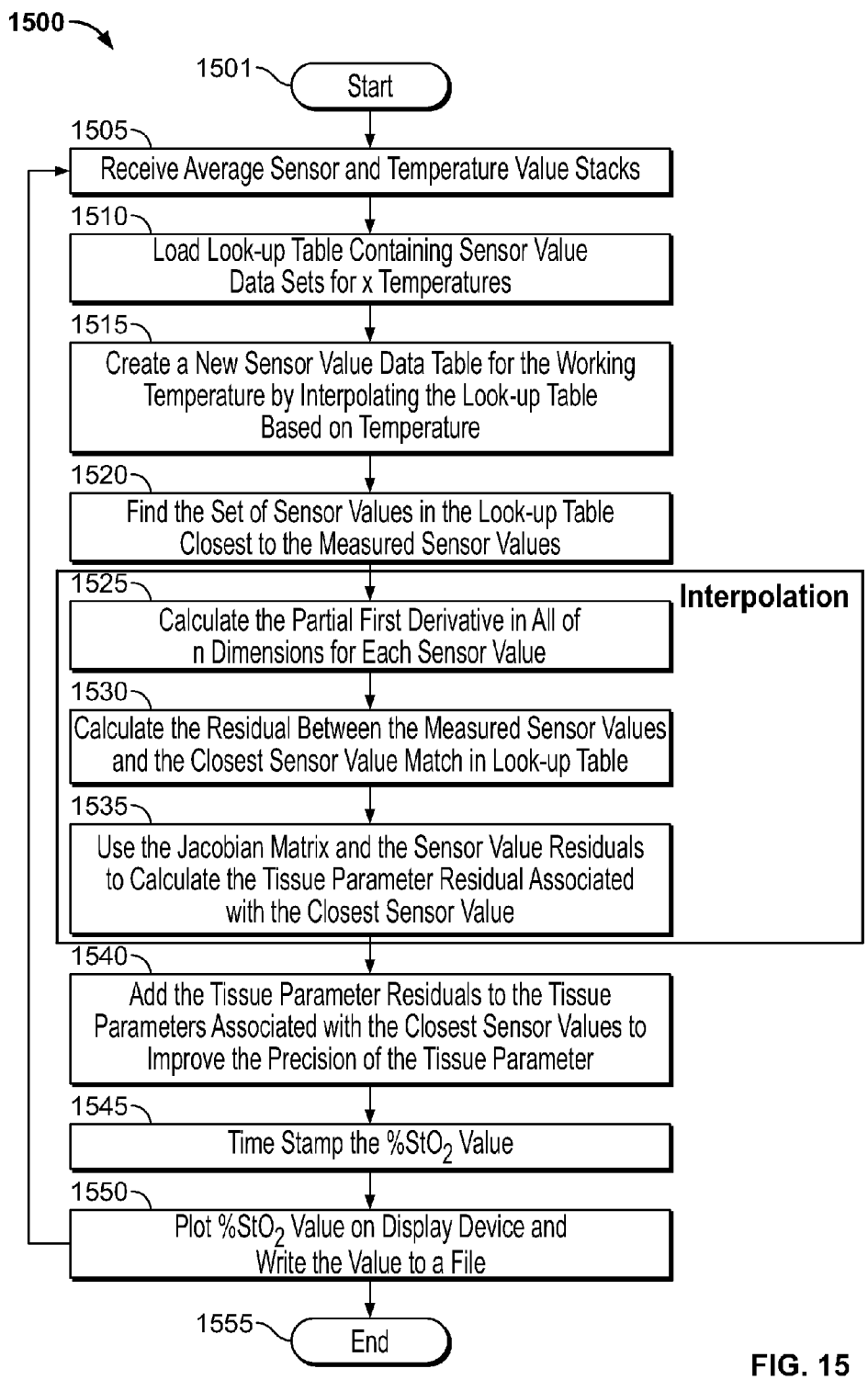
FIG. 15 shows a process for determining tissue oxygenation from measured sensor values, according to one embodiment.

Referring now to FIG. 15, a computer-implemented process 1500 for determining % $StO_2$ values is illustrated by way of the flowchart. In one embodiment, % $StO_2$ values can be determined using the sensor data readings generated in process 1400 described above in cooperation with the look-up table generated in process 1200 described with respect to FIG. 12. It will be understood that other alternative approaches may be used.

The process 1500 begins at process point 1501. Next, at step 1505, the control system 1151 receives the average sensor and temperature value stacks generated from the process for collecting sensor value data 1400 described above.

Next, at step 1510, the control system 1151 loads the look-up table generated in the process 1200 described above, which contains modeled sensor value data sets at a plurality of temperatures. In general, the plurality of temperature-dependent sensor value sets can have a temperature spacing, e.g., the first sensor value set may be modeled at 20° C., the second sensor value set can be modeled at 25° C., and so on, which can advantageously reduce the size- and the amount of Monte Carlo calculations required to generate the look-up table. In this embodiment, in order to use the measured sensor value sets, the look-up table can be interpolated based on temperature.

Thus, in this embodiment, the next step 1515 includes creating a new sensor value data table for the working (measured) temperature by interpolating the look-up table based on temperature. For example, if a look-up table includes modeled sensor value sets at 20° C. and 25° C., and the working temperature as measured by the photodiode 1141 was 24° C., the working temperature is 80% of the distance between the 20- and 25° C. sensor value sets. Thus, following this approach, the new sensor value data table is created based on an interpolation of the two temperature data sets at 80% of the distance between the two sets. This new sensor value data table is referred to above as TVSV.

Next, at step 1520, the control system 1151 searches for the closest match between the sensor values in the TVSV matrix and the sensor values in the look-up table.

Steps 1525, 1530, and 1535 are interpolation steps that can be performed to improve the precision in determining a tissue parameter of interest, e.g., % $StO_2$. In this embodiment, the approach used is to form a Jacobian matrix that includes the partial derivatives of each sensor value with respect to each tissue value at the closest-match sensor values. The Jacobian matrix and the residuals between the closest simulated sensor values and the measured sensor values sets up a system of n equations with n unknowns, which can be solved (e.g., using Newton's method) to yield a residual value (which is the difference between the closest tissue value and the actual value from which the closest actual value can be calculated) that can be added to the tissue parameter of interest (e.g., % $StO_2$) in the look-up table, to improve the precision in determining that tissue parameter. This is expressed mathematically by way of equations 26-30, above.

At step 1525, the partial first derivative is calculated in every dimension for each sensor value in the look-up table that was a closest match with the sensor values in the TVSV matrix. For example, for a given closest-match in the look-up table, the partial first derivative is calculated in the % $StO_2$, total hemoglobin, total adipose, and the optical coupling factor f (described above) dimensions.

Next, at step 1530, the residual values between the measured sensor values TVSV and the closest-match sensor values in the look-up table are calculated.

Next, at step 1535, the Jacobian matrix is used to solve the system of n equations with n unknowns, which yields a residual value. At step 1540, the residual value is added to the tissue parameters in the look-up table corresponding to the closest-match sensor values. The output of step 1540 is the improved-precision determination of the tissue value of interest, e.g., % $StO_2$.

Next, at step 1545, the % $StO_2$ value is time-stamped, and at step 1550, the control module sends the % $StO_2$ value to the user interface I/O module 1160 to be displayed on a display device, e.g., as illustrated in FIG. 9.

The process 1500 will continue to loop back to step 1505 to receive new measured sensor data values, then calculate and display the % StO2 values until a user terminates the process (step 1555) via the GUI. At such an event, the process ends at process point 1555.

A number of illustrative embodiments have been described. Nevertheless, it will be understood that various modifications may be made without departing from the spirit and scope of the various embodiments presented herein. For example, other concentrations of chromophores can be modeled and measured such as water content, melanin concentration, bilirubin concentration, and cytochrome oxidase concentration. Other geometric variations can be modeled and measured, such as epidermis thickness, dermis thickness, and muscle thickness, depth to bone, skull thickness, blood vessel wall thickness, and geometric properties of internal organs such as heart wall thickness. Other optical property variations can also be modeled and measured such as scattering properties of the tissue sample; for example, the scattering properties of a patient's skin is known to change with the age. These and other chromophore, geometry, and optical property measurements may necessitate adaptation of light source(s) and detector parameters, including, but not limited to: source wavelength, using a plurality of wavelength ranges, and a plurality of send to receive spacings. However, the same general approach using the methods described herein can be used to obtain a desired result.

In one variation, the model and approaches described herein can be used in agricultural applications for measuring ripeness of fruit and vegetables and the nutrition content of grains. Accordingly, other embodiments are within the scope of the following claims.

What is claimed is:

1. A method for measuring a tissue parameter in a tissue sample, said method comprising:
   receiving first and second scattered light intensity signals at unique locations on a selected region of tissue from light injected into said region of tissue from a light source to identify a measured light attenuation data value;
   accessing an electronic data store comprising simulated light attenuation data determined from a mathematical tissue model at discrete points over a range of two or more tissue parameters; wherein said simulated light attenuation data are a function of one or more temperature-dependent light source spectra and are determined in part by simulating a plurality of light ray paths launched from said light source into said region of tissue and detected at said unique tissue locations; wherein said simulated light attenuation data are calculated in part by integrating a modified Beer-Lambert equation over wavelength for each of said plurality of light ray paths for a given light source spectrum;
   determining said tissue parameter in said tissue sample by selecting a closest match between said measured light attenuation data and said simulated light attenuation data; and
   transmitting an electronic signal representative of said determined tissue parameter to an output register.

2. The method of claim 1, wherein said tissue parameter is a chromophore concentration within said tissue.

3. The method of claim 2, wherein said chromophore is oxyhemoglobin or deoxyhemoglobin.

4. The method of claim 1, wherein said receiving first and second light signals comprises receiving light signals generated by first and second photodiodes arranged in a confronting relationship with a surface of said tissue sample.

5. The method of claim 4, wherein said first and second photodiodes are linearly arranged with respect to said light source and evenly distributed such that the distance between said light source and said first photodiode is approximately one-half the distance between said light source and said second photodiode.

6. The method of claim 1, wherein said light source is the distal end of a solid light-transmitting medium arranged in a confronting relationship with a surface of said tissue sample, and wherein a proximal end of said light-transmitting medium is in optical communication with one or more light sources.

7. The method of claim 6, wherein said light source is a light-emitting diode (LED) configured to emit light having a selected center wavelength and a selected spectral bandwidth.

8. The method of claim 7, further comprising a plurality of LEDs adjacently arranged so as to maximize light output coupling efficiency into said proximal end of said light-transmitting medium.

9. The method of claim 6, wherein said solid light-transmitting medium is a substantially transparent, rectangular polycarbonate member having a proximal (light input) end and a distal (light output) end and a length l therebetween, wherein said polycarbonate member has a substantially square cross-section perpendicular to said length l.

10. The method of claim 1, wherein said two or more tissue parameters are selected from the group consisting of: % $StO_2$, adipose thickness, muscle thickness, dermis thickness, epidermis thickness, total hemoglobin concentration, melanin concentration, and water volume fraction.

11. The method of claim 1, wherein said selecting a closest match between said measured light attenuation data and said simulated light attenuation data comprises interpolation of said calculated light attenuation data based on a measured temperature of said light source.

12. A method for measuring a tissue parameter in a tissue sample, said method comprising:
   receiving first and second scattered light intensity signals at unique locations on a selected region of tissue from light injected into said region of tissue from a light source to identify a measured light attenuation data value;
   accessing an electronic data store comprising simulated light attenuation data determined from a mathematical tissue model at discrete points over a range of two or more tissue parameters, and wherein said simulated light attenuation data are a function of one or more temperature-dependent light source spectra;

determining said tissue parameter in said tissue sample by selecting a closest match between said measured light attenuation data and said simulated light attenuation data; and transmitting an electronic signal representative of said determined tissue parameter to an output register;

wherein said selecting a closest match between said measured light attenuation data and said calculated light attenuation data comprises:

determining a ratio value of said first and said second scattered light intensity signals from said light source;

receiving a temperature measurement of said light source;

generating a temperature-corrected set of light attenuation data by interpolating said calculated light attenuation data based on said measured temperature;

finding the closest match of said temperature-corrected set of light attenuation data in said electronic data store;

forming a Jacobian matrix that includes the partial derivatives of each temperature-corrected light attenuation data point with respect to each of said tissue parameter values at the closest-match sensor value; and solving the system of n equations and n unknowns provided by said Jacobian matrix and the residual values between said closest-match sensor value and said measured light intensity signal to yield a correction value that can be applied to said determined chromophore concentration to increase the precision of said measurement.

13. The method of claim 12, wherein said light source is configured to project the output of two or more LEDs having different output light spectral profiles, and wherein determining a ratio value of said first and said second scattered light intensity signals from said light source comprises determining a ratio value of said first and said second scattered light intensity signals at each of said output light spectral profiles.

14. The method of claim 12, further comprising adding or subtracting said correction value to said tissue parameter.

15. The method of claim 1, wherein said tissue sample is tissue of a living organism.

16. The method of claim 15, wherein said tissue is the gastrocnemius muscle of the lower leg of a human.

17. The method of claim 1, wherein said method is executed in a continual loop so as to provide a data stream of chromophore concentration measurements on a tissue sample, wherein said data stream is sent to said output register to be displayed on a display device.

18. The method of claim 17, wherein said loop has a cycle rate between about 1 second and about 3 seconds.

19. A computer program product, encoded on a non-transitory computer-readable medium, operable to cause one or more processors to perform operations for measuring a chromophore concentration in a tissue sample, comprising:

receiving first and second scattered light intensity signals at unique locations on a selected region of tissue from light injected into said region of tissue from a light source to identify a measured light attenuation data value;

accessing an electronic data store comprising calculated light attenuation data determined from a mathematical tissue model at discrete points over a range of two or more tissue parameters; wherein said chromophore is one of said parameters, and wherein said light attenuation data are a function of one or more temperature-dependent light source spectra and are determined in part by simulating a plurality of light ray paths launched from said light source into said region of tissue and detected at said unique tissue locations; wherein said simulated light attenuation data are calculated in part by integrating a modified Beer-Lambert equation over wavelength for each of said plurality of light ray paths for a given light source spectrum;

determining said chromophore concentration in said tissue sample by selecting a closest match between said measured light attenuation data and said calculated light attenuation data; and transmitting an electronic signal representative of said determined chromophore concentration to an output register.

20. A system for measuring a tissue parameter in a tissue sample, comprising:

a computer control system in signal communication with a remote sensing device, the remote sensing device comprising:

a) a plurality of light sources operable to produce an output signal for each of said light sources successively, each of said output signals having a different spectral profile than the other of said output signals, wherein said plurality of light sources is cooperatively arranged with a light-transmitting medium that is configured to inject said output signals into said tissue sample at a selected injection area of said tissue sample; and b) two or more light detectors arranged substantially collinear with said light source, wherein a distance from said light source to a first of said detectors is about one-half the distance of said light source to a second, different one of said detectors, wherein each of said detectors is configured to receive said light signal after propagating through said tissue to measure an attenuated light value;

wherein said control system is operable to initiate said measurement of said attenuated light signals; and wherein said computer control system comprises:

a) a processor in signal communication with a data store comprising simulated light attenuation values determined from a mathematical tissue model at discrete points over a range of two or more tissue parameters; wherein said simulated light attenuation values are a function of one or more temperature-dependent variables of said light source spectra and are determined in part by simulating a plurality of light ray paths launched from said light source into said region of tissue and detected at said unique tissue locations; wherein said simulated light attenuation data are calculated in part by integrating a modified Beer-Lambert equation over wavelength for each of said plurality of light ray paths for a given light source spectrum; and b) an output register in signal communication with said processor configured to receive a processor-calculated tissue parameter value determined by selecting a closest match between said measured light attenuation value and said simulated light attenuation values.

* * * * *